US009556080B2

(12) United States Patent
Toutov et al.

(10) Patent No.: US 9,556,080 B2
(45) Date of Patent: Jan. 31, 2017

(54) SILYLATION OF AROMATIC HETEROCYCLES BY DISILANES USING POTASSIUM ALKOXIDE CATALYSTS

(71) Applicant: CALIFORNIA INSTITUTE OF TECHNOLOGY, Pasadena, CA (US)

(72) Inventors: Anton Toutov, Pasadena, CA (US); Wenbo Liu, Pasadena, CA (US); Brian M. Stoltz, San Marino, CA (US); Robert H. Grubbs, South Pasadena, CA (US); Kerry Betz, Boulder, CO (US); David P. Schuman, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 14/972,653

(22) Filed: Dec. 17, 2015

(65) Prior Publication Data
US 2016/0176772 A1    Jun. 23, 2016

Related U.S. Application Data

(60) Provisional application No. 62/094,401, filed on Dec. 19, 2014, provisional application No. 62/094,443, filed on Dec. 19, 2014, provisional application No. 62/119,940, filed on Feb. 24, 2015.

(51) Int. Cl.
*C07B 47/00* (2006.01)
*C07F 7/08* (2006.01)
*C07D 209/12* (2006.01)

(52) U.S. Cl.
CPC ............. *C07B 47/00* (2013.01); *C07D 209/12* (2013.01); *C07F 7/0827* (2013.01)

(58) Field of Classification Search
CPC ............................. C07B 47/00; C07F 7/0827
See application file for complete search history.

(56) References Cited

U.S. PATENT DOCUMENTS

| | | | |
|---|---|---|---|
| 4,360,686 | A | 11/1982 | Wang et al. |
| 4,363,925 | A | 12/1982 | Acker et al. |
| 5,516,908 | A | 5/1996 | Freyne et al. |
| 9,000,167 | B2 | 4/2015 | Grubbs et al. |
| 2015/0166579 | A1 | 6/2015 | Grubbs |

FOREIGN PATENT DOCUMENTS

WO    WO 2014/055587 A1    4/2004

OTHER PUBLICATIONS

Watanabe et al. "Simple and convenient method for preparing functionalized network organopolysilanes" Journal of Materials Chemistry, 1991, vol. 1, pp. 483-484.*

Shippey et al. "Trimethylsilyl Anions. Direct Synthesis of Trimethylsilylbenzenes", Journal of Organic Chemistry, 1997, vol. 42, pp. 2654-2655.*
Aikawa, et al., "Highly Enantioselective Alkynylation of Trifluoropyruvate with Alkynylsilanes Catalyzed by the BINAP—Pd Complex: Access to a-Trifluoromethyl-Substituted Tertiary Alcohols", Org. Lett., Nov. 16, 2010, 12(24), 5716-5719.
Anastas, et al., "Origins, Current Status, and Future Challenges of Green Chemistry", Chem. Res. 2002, vol. 35(9), 686-694.
Andreev, et al., "Direct Electrophilic Silylation of Terminal Alkynes", Organic Letters, Jan. 15, 2004, vol. 6(3), 421-424.
Babudri, et al., "A Straightforward Route to Polyenylsilanes by Palladium-Catalyzed or Nickel-Catalyzed Cross-Coupling Reactions", Tetrahedron, 1998, 54(7),1085-1094.
Ball, et al., Science, "Gold-Catalyed Direct Arylation", Sep. 28, 2012, vol. 337(102), 1644-1648.
Bekele, et al., "Improved Synthesis of the Boc and Fmoc Derivatives of 4-(2'-Aminoethyl)-6- dibenzofuranpropionic Acid: An Unnatural Amino Acid That Nucleates .beta.-Sheet Folding", Journal of Organic Chemistry, 1997, 62, 2259-2262.
Bergman, et al., Organometallic chemistry: C—H activation, Nature, Mar. 2007, vol. 446, 391-393.
Cheng, et al., "Rhodium-Catalyzed Intermolecular C—H Silylation of Arenes with High Steric Regiocontrol", Science, Feb. 2014, 343(6173), 853-857.
Cheng, et al., "Synthesis of Conjugated Polymers for Organic Solar Cell Applications", Chem. Rev., Sep. 2009, vol. 109(11), 5868-5923.
Cheve et al., "De Novo Design, Synthesis and Pharmacological Evaluation of New Azaindole Derivatives as Dual Inhibitors of Abl and Src kinases", Med Chem Comm, 2012, 3, 7, 788-800.
Chinchilla, et al., "Recent Advances in Sonogashira Reactions", Chem. Soc. Rev., Mar. 18, 2011, 40, 5084-5121.
Clark, et al., "Green Chemistry: Challenges and Opportunities", Green Chem., Feb. 1999, vol. 1, 1-8.
Collins, et al., "A Robustness Screen for the Rapid Assessment of Chemical Reaction", Nature Chem., Jun. 2013, 5, 597-601.
Curless, et al., "E-H (E=R3Si or H) Bond Activation by B(C6F5)3 and Heteroarenes; Competitive Debydrosilylation, Bydrosilyiation and Hydrogenation", Chem. Commun., Nov. 2013, 50, 5270-5272.
Denmark, et al., Palladium-Catalyzed Cross-Coupling Reactions of Silanolates: a Paradigm Shift in Silicon-Based Cross-Coupling Reactions. Chem. Eur., 2006, 2, 4954-4963.
Despotopoulou, et al., "Synthesis of Fully Substituted Pyrazoles via Regio- and Chemoselective Metalations", P. Org. Lett., Jul. 2009, 11(15), 3326-29.
Diez-Gonzalez, et al. , "Copper, Silver, and Gold Complexes in Hydrosilylation Reactions", Accounts of Chemical Research, vol. 41(2), Feb. 2008, 349-358.
Du, et al., "Semisynthesis of DB-6 7 and Other Silatecans from Camptotbecin by Thiol-Promoted Addition of Silyl Radicals", Bioorg. Med. Chem., Feb. 2003, 11(3), 451-458.
Dudziec, et al., "New Catalytic Route to Monoalkynyl-Functionalized Di and Trivinyl-Substituted Cyclosiloxanes and Divinylcyclosilazanes", Organometallics, Oct. 2008, vol. 27(21), 5598-5604.

(Continued)

*Primary Examiner* — Joseph Kosack
(74) *Attorney, Agent, or Firm* — Baker & Hostetler LLP

(57) ABSTRACT

The present invention describes chemical systems and methods for silylating heteroaromatic organic substrates, said system consisting essentially of a mixture of (a) at least one organodisilane and (b) at least alkoxide base, preferably a potassium alkoxide base, and said methods comprising contacting a quantity of the organic substrate with a mixture consisting essentially of (a) at least one organodisilane and (b) at least one alkoxide base, preferably a potassium alkoxide, under conditions sufficient to silylate the heteroaromatic substrate.

46 Claims, 1 Drawing Sheet

(56) References Cited

OTHER PUBLICATIONS

Eaborn, Cleavages of Aryl-Silicon and Related Bonds by Electrophiles, J. Organomet. Chem., Oct. 1975, vol. 100(1), 43-57.

Fedorov, et al., "Lewis-Base Silane Activation: From Reductive Cleavage of Aryl Ethers to Selective Ortho-Silylation", Chem. Sci., Feb. 2013, 4, 1640-1645.

Franz, et al., "Organosilicon Molecules with Medicinal Applications", J Med. Chem.,Oct. 2012, 56(2), 388-405.

Frick, et al, "Elektrophile Silylierung Elektronenreicher Heteroaromaten", Synthesis, Nov. 1984, 929-930.

Fujiki, "Optically Active Polysilanes. Ten Years of Progress and New Polymer Twist for Nanoscience and Nanotechnology", Polymer Journal, 2003, vol. 35(4), 297-344.

Furukawa, et al., "Development of a Sila-Friedel-Crafts Reaction and its Application to the Synthesis of Dibenzosilole Derivatives", J. Am. Chem. Soc., Sep. 2009, 131(40), 14192-14193.

Gleiter, et al., "Alkynes Between Main Group Element: From Dumbbells via Rods to Squares and Tubes", Chem. Rev., Apr. 14, 2010, 110, 4447-88.

Godula, et al., "C—H Bond Functionalization in Complex Organic Synthesis", Science, 2006, vol. 312, 67-72.

Habich, et al., "Preparation of Aryl- and Heteroaryltrimethylsilanes", Reviews, 1979, 841-876.

Hansen, et al., "Lithiated Benzothiophenes and Benzofurans Require 2-Silyl Protection to Avoid Anion Migration", Revue, 2004, 8, 1351-1354.

Huckins, et al., "Synthesis of Optically Pure Arylsilylcarbinols and Their Use as Chiral Auxiliaries in Oxacarbenium Ion Reactions", Journal of Organic Chemistry, 2003, 68, 10135-10145.

Huestis, et al., "Site-Selective Azaindole Arylation at the Azine and Azole Rings via N-Oxide Activation", Org Lett., Mar. 2009, 11(6), 1357-60.

Ishikawa, et al., "Dehydrogenative Coupling Between Hydrosilanes and Alkynes Catalyzed by Alkoxided, Alkylmetals, and Metalamides", Journ. of Catalysis, Apr. 16, 1999, 185,454-61.

Islam, et al., "On water, Phosphine-Free Palladium-Catalyzed Room Temperature C—H Arylation of Indoles.", Chem. Eur. J., 2013, 19, 15093-15096.

Isogai, et al., "CUX2-Mediated [4+2] Benzannulation as a New Synthetic Tool for Stereoselective Construction of Haloaromatic Compounds", Tetrahedron, 65, Sep. 2009, 9575-82.

Itami, et al., "2-Pyridylsilyl Group: A Useful Multifunctional Group in Organic Synthesis", Synlett, Dec. 2005, 2, 157-180.

Itoh, "Disproportionation Reactions of Organohydrosilanes in the Presence of Base Catalysts", Journ. of Organo Metalic Chem., 629, Feb. 2001, 1-6.

Itoh, et al., "Dehydrogenative Coupling Reactions Between Hydrosilanes and Monosubstituted Alkynes Catalyzed by Solid Bases", Journ. of Organo. Chem., 476, 1994, C30-C31.

Kakiuchi, et al., "Ru3 (C0) $_{12}$—Catalyzed Silylation of Benzylic C—H Bonds in Arylpyridines and Arylpyrazoles with Hydrosilanes via C—H Bond Cleavage", J A.M. Chem. Soc., Sep. 2004, 126(40), 12792-12793.

Kaur, et al., "(NHC)CuI (NHC = N-Heterocyclic Carbene) Complexes as Efficient Catalysts for the Reduction of Carbonyl Compounds", Organometallics, 2004, 23(5), 1157-1160.

Keaton, et al., "Titanium(II)-Mediated Cyclization of (Silyloxy)enynes: A Total Synthesis of (−)-7-Demethylpiericidin A1", JACS, Dec. 17, 2005, 408-409.

Kim, et al., "Regio- and Stereoselective Enyne Cross Metathesis of Silylated Internal Alkynes", JACS, Aug. 3, 2004, 10242-43.

Klare, et al., "Cooperative Catalyic Activation of Si—H bonds by a Polar Ru—S Bond: Regioselective Low-Temperature C—H Silyiation of Indoles Under Neutral Conditions by a Friedel-Crafts Mechanism", J. Ant Chem. Soc., Feb. 2011, 133(10), 3312-3315.

Kong, et al., "Highly Efficient Construction of Benzene Ring in Carbazoles by Palladium-Catalyzed Endo-Mode Oxidative Cyclization of 3-(3'-alkenyl)indoles.", Org. Lett., 2006, 8, 1339-1342.

Konigs, et al, "Base-Free Dehydrogenative Coupling of Enolizable Carbonyl Compounds with Silanes", Org. Lett., 2012, vol. 14(11), 2842-2845.

Kuznetsov, et al., "Fused Heteroaromatic Dihydrosiloles: Synthesis and Double-Fold Modification", Org. Lett., Apr. 2013, 15(10), 2498-2501.

Kuznetsov, et al., General and Practical One-Pot Synthesis of Dihydrobenzosiloles from Styrenes, Org. Lett., Jan. 2012, 14(3), 914-917.

Langkopf, et al., "Uses of Silicon-Containing Compounds in the Synthesis of Natural Products", Chem. Rev., Jul. 1995, 95(5), 1375-1408.

Lee, et al., "Highly Selective and Practical Hydrolytic Oxidation of Organosilanes to Silanols Catalyzed by a Ruthenium Complex", J Am. Chem. Soc., 2000, 122(48), 12011-12012.

Li, et al., "Green Chemistry f(Ir chemical Synthesis", Proc. Natl Acad. Sci., 2008, 105, 13197-13202.

Li, et al., "Green chemistry: The Development of Cross-Dehydrogenative Coupling (CDC) for Chemical Synthesis", Pure Appl., 2006, Chem. 78(5), 935-945.

Lu, et al., "Efficient Iridium-Catalyzed C—H Functionalization/ Silylation of Heteroarenes", Angew. Chem., Int. Ed., Aug. 2008, 47(39), 7508-7510.

Mahadevan, et al., "Ambident Heterocyclic Reactivity: The Alkylation of Pyrrolopyridines (azaindoles, diazaindenes)", Aug. 1993, 49(33), 7337-52.

Marsden, et al. Structure-Property Relationships of Donor Acceptor-Functionalized Tetrakis(phenylethynyl)benzenes and Bis(dehydrobenzoannuleno)benzenes, J. Am. Chem. Soc., Feb. 2005, 2464-76.

Mita, et al., "Sequential Protocol for C(sp3_-H Carboxylation with CO2: Transition—Metal-Catalyzed Benzylic C—H Silylation and Fluoride-Medicated Carboxylation", Organic Letters, Jun. 19, 2012, vol. 14(13), 3462-3465.

Miyaura, "Organoboron Compounds", Top. Curr. Chem., Jan. 2002, 219, 11-59.

Miyaura, et al., "Palladium-Catalyzed Cross-Coupling Reactions of Organoboron Compounds", A. Chem. Rev. 1995, 95(7), 2457-2483.

Mu, et al. "Silicon-Based Building Blocks for One-Step 18F-Radiolabeling of Peptides for PET Imagin", Angew Chem., 2008, 47, 4922-25.

Nishihara, et al., "Palladium/Copper-Catalyzed Sila-Sonogashira Reactions of Aryl Iodides with Alkynylsilanes via a Direct C—Si Bond Activation", Tetrahedron Letters, 50, Jun. 2009, 4643-4646.

Oyamada, et al., "Scandium-Catalyzed Silylation of Aromatic C—H bonds", Angew. Chem. Int. Ed., Sep. 2011, 50, 10720-10723.

Park, et al., "Transition Metal-Catalyzed Ortho-Functionalization in Organic Synthesis", Bull. Korean Chem. Soc., 2005, vol. 26(6), 871-877.

Park, et al., "Gold-Catalyzed Intramolecular Allylation of Silyl Alkynes Induced by Silane Alcoholysis" JACS, 128, 10664-10665, Jul. 28, 2006, 10664-65.

Rahaim, et al., "Zinc-Catalyzed Silylation of Terminal Alkynes", J. Org. Chem., Mar. 11, 2008, vol. 73, 2912-2915.

Rychnovsky et al., "Synthesis of Optically Pure Arylsilylcarbinols and Their Use as Chiral Auxiliaries in Oxacarbenium Ion Reactions", Journal of Organic Chemistry, 2003, 68, 10135-10145.

Sakakura, et al., "Catalytic C—H Activation. Silylation of Arenes with Hydrosilane or Disilane by RhCl (CO)(PMe) $_2$ Under Irradiation", Chem. Lett., 1987,16(12), 2375-2378.

Scheuermann, "Beyond Traditional Cross Couplings: The Scope of the Cross Dehydrogenative Coupling Reaction", Chem. Asian J., Dec. 2009, vol. 5, 436-451.

Seiple, et al., "Direct C—H Arylation of Electron-Deficient Heterocycles with Arylboronic Acids", J. Am. Chem. Soc., Sep. 2010, 132(38), 13194-13196.

Seregin, et al., "Direct Transition Metal-Catalyzed Functionalization of Heteroaromatic Compounds", Chem. Soc. Rev., Mar. 2007, 36, 1173-1193.

Shimizu, et al., "Dehydrogenative Silylation of Terminal Alkynes by Iridium Catalyst", Tet. Lett., 2000, vol. 41, 907-910.

(56) References Cited

OTHER PUBLICATIONS

Showell, et al., "Chemistry Challenges in Lead Optimization: Silicon Isosteres in Drug Discovery", Drug Discov., Jun. 2003, 8(12), 551-556.
Song, et al., "Organometallic Methods for the Synthesis and Functionalization of Azaindoles", Chem. Soc. Rev., Feb. 2007, 36, 1120-1132.
Starkov, et al., "Catalytic Electrophilic Halogenation of Siyl-Protected and Terminal Alkynes: Trapping Gold (I) Acetylides vs. a Bronsted Acid-Promoted Reaction", Adv. Synth. Catal., Nov. 2012, 354, pp. 3217-3224.
Sugita, et al., "A Novel Reduction of Zinc(II) Chloride with Samarium Metal and its Application to Silylation of 1-Alkynes. Synlett", 1996, vol. 7, 637-639.
Tamao, et al., "Silole Derivatives as Efficient Electron Transporting Materials", J. Am. Chem. Soc., Nov. 1996, 118(47), 11974-11975.
Ting, et al., "Arylfuoroborates and Alkylfluorosilicates as Potential PET Imaging Agents: High-Yielding Aqueous Biomolecular 18F-Labeling", J. Am. Chem. Soc., Sep. 2005, 127(38), 13094-13095.
Toutov, et al., "Silylation of C—H Bonds in Aromatic Heterocycles by an Earth—Abundant Metal Catalyst", Nature, Feb. 2015, 518, 80-84.
Tsuchimoto, et al., "Dehydrogenative Silylation of Terminal Alkynes with Hydrosilanes under Zinc—Pyridine Catalysis", Adv. Synth. Catal., 2012, vol. 354, 2959-2964.
Ulrich, et al., "Elektrophile Silyberung Elektronemrelcher Heteroaromaten", Synthesis, Nov. 1984, 929-930.
Voronkov, et al., "Dehydrocondensation of Trialkylsilanes with Acetylene and Monosubstituted Acetylenes", J. Organomet. Chem., 1984, vol. 264, 39-48.
Wang, et al., "Transition-Metal-Free Synthesis of Alternating Thiophene-Perfluoroarene Copolymers", J. Am. Chem. Soc., Feb. 2006, 128(8), 2536-2537.
Wang, et al., "Unique σ-Bond Metathesis of Silylalkynes Promoted by an ansa-Dimethylsilyl and Oxo-Bridged Uranium Metallocene", J. Am. Chem. Soc., Jun. 2006, vol. 128(29), 9350-9351.
Weickgenannt, et al., "Potassium tert-Butoxide-Catalyzed Dehydrogenative Si—O Coupling: Reactivity Patten and Mechanism of an Underappreciated Alcohol Protection", Chem. Asian J., Jan. 2009, 4(3), 406-410.
Whisler, et al., "Beyond Thermodynamic Acidity: A Perspective on the Complex-Induced Proximity Effect (CIPE) in Deprotonation Reactions", Angew. Chem., Int Ed., Apr. 2004, 43(17), 2206-2225.
Yamaguchi, et al., "Heterogeneously Catalyzed Aerobic Cross-Dehydrogenative Coupling of Terminal Alkynes and Monohydrosilanes by Gold Supported on OMS-2", Angew Chem., 2013, 52, 5627-30.
Zhang, et al., "Thiophene-Based Conjugated Oligomers for Organic Solar Cells", J. Mater. Chem., Sep. 2011, 21, 17590-17600.
Zhao, et al., "Directed *Ortho* Metalation-Based Methodology. Halo-, Nitroso-, and Boro-Induced *ipso*-Desilylation. Link to an in situ Suzuki Reaction", Org. Lett., May 2005, 7(13), 2523-2526.
Dervan, et al., "Trimethylsilylpotassium. Deoxygenation of Epoxides With Inversion of Stereochemistry", J. Am. Chem. Soc., 1976, vol. 98, 1265-1267.
Haebich, et al., "Preparation of Aryl-and Heteroaryltrimethylsilanes", Synthesis, 1979, Issue 11, 841-876.
Kyalo, et al., "Palladium-catalyzed Direct C—H Silylation and Germanylation of Benzamides and Carboxamides", Org. Lett., 2014, vol. 16, 1968-1971.
Shippey, et al., "Trimethylsilyl Anions. Direct Synthesis of Trimethylsilybenzenes", J. Org. Chem., 1977, vol. 42, 2654-2655.

* cited by examiner

SILYLATION OF AROMATIC HETEROCYCLES BY DISILANES USING POTASSIUM ALKOXIDE CATALYSTS

CROSS REFERENCE TO RELATED APPLICATIONS

This application claims priority to U.S. Patent Application No. 62/094,401, filed Dec. 19, 2014; 62/094,443, also filed Dec. 19, 2014 and 62/119,940, filed Feb. 24, 2015, the contents of which are all incorporated by reference herein for all purposes.

GOVERNMENT RIGHTS

This invention was made with government support under Grant No. CHE-1205646 and under Grant No. CHE-1212767 awarded by the National Science Foundation. The government has certain rights in the invention.

TECHNICAL FIELD

The present invention is directed at methods for silylating aromatic substrates, including heteroaromatic substrates, using alkoxides (especially potassium alkoxide) and disilane reagents.

BACKGROUND

The ability to silylate organic moieties has attracted significant attention in recent years, owing to the utility of the silylated materials in their own rights or as intermediates for other important materials used. Applications for these materials are important in agrichemical, pharmaceutical, and electronic material applications. Further, the ability to functionalize polynuclear aromatic compounds with oganosilanes provides opportunities to take advantage of the interesting properties of these materials.

At present, the most common approach to heteroaromatic C—Si bond construction involves the interception of heteroaryl lithium or magnesium reagents with silicon electrophiles. However, this method is often limited in scope and requires prefunctionalization of heteroarenes by using pyrophoric organometallic species in stoichiometric quantities. Powerful heteroaromatic functionalization strategies, such as Minisci-type radical substitutions and Friedel-Crafts reactions, have been of limited use for C—Si bond construction owing to the difficulty of generating the corresponding silyl radicals and silylium ions.

More recently, the transition metal mediated aromatic C—H silylation has been described, with different systems described based on, for example, Co, Rh, Ir, Fe, Ru, Os, Ni, Pd, and Pt catalysts. But certain electronic applications, the presence of even low levels of such residual can adversely affect the performance of the silylated materials. Similarly, in certain pharmaceutical or electronic applications, limits on residual transition metals are fairly strict, and the ability to avoid them entirely offers benefits during post-synthesis work-up.

The present invention takes advantage of the discoveries cited herein to avoid at least some of the problems associated with previously known methods.

SUMMARY

The present disclosure provides new information with respect to the alkoxide catalyzed silylation of heteroaromatic substrates. It has now been found that alkoxides, especially potassium alkoxides, can be an effective catalyst for the direct silylation of heteroaromatic substances with organodisilanes under certain conditions. The use of organodisilanes offers important practical benefits over hydrosilane synthons including easier handling of the organodisilanes relative to the much more volatile hydrosilanes.

Various embodiments of the present invention provide chemical systems for silylating organic compounds, each system comprising or consisting essentially of a mixture of (a) at least one organodisilane and (b) at least one alkoxide base, preferably potassium alkoxides, and more preferably potassium ethoxides or tert-butoxides, said system also operable to silylate a heteroaromatic precursor. The presence of transition metal silylation catalysts are not required and in certain embodiments, such systems are substantially free of a transition-metal compound. The system may further comprise at least one organic heteroaromatic substrate to be silylated.

Other embodiments provide methods, each method comprising contacting the organic heteroaromatic substrate with a mixture comprising or consisting essentially of (a) at least one organodisilane and (b) at least one alkoxide base, preferably potassium alkoxides, and more preferably potassium ethoxides or tert-butoxides, under conditions sufficient to silylate the substrate. In some embodiments, said mixture and substrate are preferably, but not necessarily, substantially free of a transition-metal compound.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION OF ILLUSTRATIVE EMBODIMENTS

Figure 1:
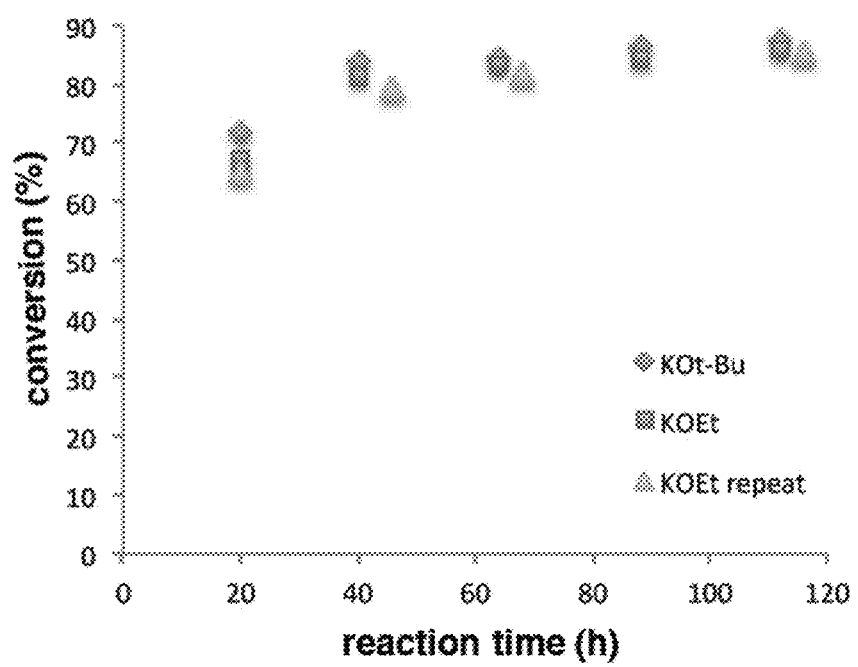
FIG. 1 presents data showing the reproducibility of conversion as a function of reaction time for some of the inventive systems.

The present invention is founded on a set of reactions, each of which relies on simple mixtures of organodisilanes and at least one alkoxide base, preferably at least one potassium alkoxide, and more preferably potassium ethoxide or tert-butoxide, which together form in situ systems (the structure and nature of the active species is still unknown) able to silylate heteroaromatic molecules in the liquid phase, without the need for transition metal silylation catalysts, UV radiation or electrical (including plasma) discharges. These reactions are relevant as an important advance in developing practical methods for the preparation of products important for pharmaceutically and electronics applications. Importantly this reaction is of great interest since it produces only environmentally benign silicates and dihydrogen as the byproduct and can avoid toxic metal waste streams as would be observed with nearly all other approaches proposed in the literature towards this end. The remarkable facility and regiospecificity exhibited by at least some of these systems provides a useful tool in the kit of chemists in these fields.

The silylation reactions described herein proceed under mild conditions, in the absence of hydrogen acceptors, ligands or additives, and is scalable to greater than 100 grams. Substrate classes that are difficult to activate with precious metal catalysts are silylated in good yield and with excellent regioselectivity. The derived heteroaryl silane products readily engage in versatile transformations enabling new synthetic strategies for heteroaromatic elaboration, and are useful in their own right in pharmaceutical and materials science applications.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods (or the systems used in such methods or the compositions derived therefrom) to silylate heteroaromatic organic moieties. In those embodiments that provide a system or method comprises the use of a mixture consisting essentially of the substrate, organodisilane, and alkali metal alkoxide base (preferably potassium alkoxides, and more preferably potassium ethoxides or tert-butoxides), it refers to the fact that this system operates to silylate the substrate at rates roughly corresponding to those described herein under comparable conditions as described herein without additional (e.g., transition metal silylation) catalysts or plasma or UV radiation sources. While some level of transition metal compounds may be present, they are not needed for the operability of the methods, and may be considered spectators for purposes of this reaction. Similarly, while other previous silylation reactions have employed plasma or UV irradiation to operate, the present invention does not require these energy sources. The additional presence of these energy sources should not be seen as replacing the basis underlying operability of the present methods.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, a designation such as $C_{1-3}$ includes $C_1$, $C_2$, $C_3$, $C_{1-2}$, $C_{2-3}$, $C_{1,3}$, as separate embodiments, as well as $C_{1-3}$.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, tert-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or prepolymeric (e.g., monomeric, dimeric), oligomeric or polymeric analogs thereof.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2, 7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)—alkyl, —O(CO)-aryl, or —O(CO)-aralkyl, wherein "alkyl," "aryl, and "aralkyl" are as defined above.

The terms "cyclic" and "ring" refer to alicyclic (including saturated or unsaturated) or aromatic groups that may or may not be substituted and/or heteroatom-containing, and that may be monocyclic, bicyclic, or polycyclic. The term "alicyclic" is used to describe a cyclic moiety that may be monocyclic, bicyclic, or polycyclic.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the terms "substrate" or "organic substrate" are intended to connote both discrete small molecules (sometimes described as "organic compounds"), oligomers, and polymers containing such "heteroaromatic moieties." The term "heteroaromatic moieties" is intended to refer to those portions of the compounds, pre-polymers (i.e., monomeric compounds capable of polymerizing), oligomers, or polymers having at least one of the indicated heteroaromatic structures. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl),N—($C_5$-$C_{24}$ aryl)-substituted carbamoyl, thiocarbamoyl (—(CS)—$NH_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl),N—($C_5$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR═NH where R=hydrogen, $C_1$-$C_{24}$ alkyl, C5-C24 aryl, $C_6$-$C_{24}$ alkaryl, $C_6$-$C_{24}$ aralkyl, etc.), $C_2$-$C_{20}$ alkylimino (—CR═N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2OH$), sulfonate ($SO_2O$—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl-$SO_2$—N(H) alkyl), $C_1$-$C_{24}$ dialkylaminosulfonyl-$SO_2$—N(alkyl)$_2$, $C_5$-$C_{24}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—$PO_2$), and phosphine (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Again, each of these options and any combination thereof, is considered to reflect a separate embodiment of the present disclosure. Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl](DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyl-oxycarbonyl (FMOC), acetyl (Ac), benzoyl (Bz), benzyl (Bn), carbamate, p-methoxybenzyl (PMB), 3,4-dimethoxy-benzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline. Preferred substituents are those identified herein as not or less affecting the silylation chemistries, for example, including those substituents comprising alkyls; alkoxides, aryloxides, aralkylalkoxides, protected carbonyl groups; aryls optionally substituted with F, Cl, —$CF_3$; epoxides; N-alkyl aziridines; cis- and trans-olefins; acetylenes; pyridines, primary, secondary and tertiary amines; phosphines; and hydroxides.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

As used herein, the term "silylating" refers to the forming of a carbon-silicon bond in a position previously occupied by a carbon-hydrogen bond, including a non-activated C—H bond. The ability to replace directly a C—H bond with a C—Si bond, with organodisilanes under the conditions described herein, is believed to be unprecedented.

The present invention includes embodiments related chemical systems and methods for silylating heteroaromatic compounds and heteroaromatic moieties. Specific embodiments provide chemical systems for silylating heteroaromatic compounds and heteroaromatic moieties, each system comprising a mixture of (a) at least one organodisilane and (b) at least one alkoxide base, preferably a potassium alkoxide, and more preferably potassium ethoxide or tert-butoxide, said system. The presence of transition-metal silylation catalysts are not required, and in some embodiments, the systems and methods are substantially free of a transition-metal silylation catalysts or compounds.

The present inventors have previously reported the ability to silylate organic heteroaromatic moieties using various bases (including hydroxides, alkoxides, and hydrides) and hydrosilanes. See, e.g., U.S. patent application Ser. Nos. 14/043,929 and 14/818,417, which are incorporated by reference herein for all purposes. The mechanism by which these systems and methods operate is not yet understood.

Preliminary mechanistic investigations of those hydrosilane systems, at least for the silylation of heteroaromatics suggested the involvement of radical species. An elementary silyl radical generation-substitution mechanism seems to be unlikely owing to poor reactivity with electron deficient heteroarenes, such as pyridine. Moreover, the rate of silylation was greater in sulphur-containing heteroarenes than in oxygen-containing heteroarenes, and was greater in oxygen-containing heteroarenes than in nitrogen-containing heteroarenes, as observed in an internal competition study, which provided complementary reactivity to electrophilic substitutions and Minisci-type reactions. These observations pointed to an underlying mechanism that is distinct from known heteroaromatic C—H functionalization reactions. Further, the presence of hydrogen as a by-product suggested the importance of the Si—H bond in the silylation manifold.

The ability, then, to silylate such substrates using organo-disilanes was completely unexpected. Moreover, the differences in certain reactivity profiles (for example, the apparent present facile silylation of a pyridine derivative suggest a slightly different, perhaps complementary, reaction manifold.

As used herein, the term "substantially free of a transition-metal compound" is intended to reflect that the system is effective for its intended purpose of silylating heteroaromatic compounds and heteroaromatic moieties under the relatively mild conditions described herein, even in the absence of any exogenous (i.e., deliberately added or otherwise) transition-metal catalyst(s). While certain embodiments provide that transition metals, including those capable of catalyzing silylation reactions, may be present within the systems or methods described herein at levels normally associated with such catalytic activity, the presence of such metals (either as catalysts or spectator compounds) is completely unnecessary and in many cases is not desirable. As such, in preferred embodiments, the system and methods are "substantially free of transition-metal compounds." Unless otherwise stated, then, the term "substantially free of a transition-metal compound" is defined to reflect that the total level of transition metal within the silylating system, independently or in the presence of organic substrate, is less than about 100 ppm. Additional embodiments also provide that the concentration of transition metals is less than about 10 wt %, 5 wt %, 1 wt %, 100 ppm, 50 ppm, 30 ppm, 25 ppm, 20 ppm, 15 ppm, 10 ppm, or 5 ppm to about 1 ppm or 0 ppm. As used herein, the term "transition metal" is defined to include Co, Rh, Ir, Fe, Ru, Os, Ni, Pd, Pt, Cu, or combinations thereof.

In other embodiments, such transition metals may be present. In these cases, again, the presence of such metals is not required for the reactions to proceed, and in these cases, the metals may be considered to be spectators to the instant reactions. Even in those cases where the transition metals are known to catalyze silylation reactions, at best they may provide a parallel competitive reaction pathway.

Experiments with organodisilane reagents in the present system reveals a more selective requirement of solvents, than with hydrosilanes, at least under the conditions tested, appearing to require or at least prefer the presence of solvents having an oxygen donor group (e.g., non-tertiary ethers, alkylphosphoramides including HMPA, DME, THF, 2-methyl-THF, dioxanes), provided the solvent is non-reactive under the reactions conditions. See, e.g., Example 3, Table 2. However, the operability of the methods may not be limited to these types of solvents.

While it may not be necessary to limit the system's exposure to water and oxygen, in some embodiments, the chemical systems and the methods are done in an environment substantially free of water, oxygen, or both water and oxygen. In other embodiments, air and/or water are present. Unless otherwise specified, the term "substantially free of water" refers to levels of water less than about 500 ppm and "substantially free of oxygen" refers to oxygen levels corresponding to partial pressures less than 1 torr. Where stated, additional independent embodiments may provide that "substantially free of water" refers to levels of water less than 1.5%, 1%, 0.5%, 1000 ppm, 500 ppm, 250 ppm, 100 ppm, 50 ppm, 10 ppm, or 1 ppm and "substantially free of oxygen" refers to oxygen levels corresponding to partial pressures less than 50 torr, 10 torr, 5 torr, 1 torr, 500 millitorr, 250 millitorr, 100 millitorr, 50 millitorr, or 10 millitorr. In the General Procedure described herein, deliberate efforts were made to exclude both water and oxygen, unless otherwise specified.

As used herein to describe the systems and methods, the terms "organodisilane" and "disilane" are used interchangeably and refer to a compound or reagent having at least one Si—Si bond. These terms include those embodiments where the disilane contains at least one Si—H bond and those embodiments wherein the disilane no silicon-hydrogen (Si—H) bonds. While the present disclosure refers to the reaction of compounds having Si—Si bonds, the optional presence of Si—H bonds may allow the reaction to proceed through reaction manifolds previously described for silylations using hydrosilane reagents. Such a Si—H pathway is not required for silylation to proceed in the disilane systems, but where the silylating reagent contains both a Si—Si and Si—H bond, the reactions may operate in parallel with one another. The organodisilane may further contain a silicon-carbon, a silicon-oxygen, a silicon-nitrogen bond, or a combination thereof, and may be monomeric, or contained within an oligomeric or polymeric framework, including being tethered to a heterogeneous or homogeneous support structure. In certain embodiments, these organodisilane may comprise at least one compound of Formula (I) or Formula (II):

(R)$_3$Si—Si(R)$_3$     (I)

where:
each R is independently H, optionally substituted $C_{1-12}$ alkyl or heteroalkyl, optionally substituted $C_{5-20}$ aryl or $C_{4-20}$ heteroaryl, optionally substituted $C_{6-30}$ alkaryl or $C_{4-30}$ heteroalkaryl, optionally substituted $C_{6-30}$ aralkyl or $C_{4-30}$ heteroaralkyl, optionally substituted —O—$C_{1-12}$ alkyl or heteroalkyl, optionally substituted —O—$C_{5-20}$ aryl or —O—$C_{4-20}$ heteroaryl, optionally substituted —O—$C_{6-30}$ alkaryl or —O—$C_{4-30}$ heteroalkaryl, or optionally substituted —O—$C_{6-30}$ aralkyl or —O—$C_{4-30}$ heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. Exemplary, independent and non-limiting organodisilanes include (R)$_3$Si—Si(R)$_3$, where R is independently $C_{1-6}$ alkyl, preferably methyl, ethyl, propyl, tert-butyl, benzyl, aryl or heteroaryl. In some embodiments, at least one R may be hydrogen. In other embodiments, no R is hydrogen. The use of organodisilanes wherein at least one R is hydrogen may provide for opportunities for coupling or bridging reactions.

As used herein, the term "alkoxide" carries its conventional meaning, as the conjugate base of an organic alcohol. In contrast to silylating systems involving hydrosilanes, reported by the present inventors (see, e.g., U.S. patent application Ser. Nos. 14/043,929 and 14/818,417), silylations using organodisilanes appears much more selective, at least preferring, if not requiring, alkoxides, especially potassium alkoxides, to operate. Whereas hydrosilanes were shown to be operable using bases including alkali or alkaline metal hydrides, alkoxide, hydroxides, alkyl lithium compounds or amide ions, for example potassium bis(trimethylsilyl) amide, the present work shows that organodisilanes prefer or require potassium alkoxides, at least under the reaction conditions tested.

Useful alkoxides include those comprising a $C_{1-12}$ linear or branched alkyl moietird or a $C_{5-10}$ aromatic or $C_{4-10}$ heteroaromatic moieties, for examples methoxide, ethoxide, propoxide, tert-butoxide, 2-ethyl-hexyloxide, or benzyloxide. Further, the choice of the counter cation also impacts the effectiveness of the activity of the chemical system, such that potassium is preferred. Indeed, under the reaction conditions tested, reactivity required the presence of potassium cations. More specifically, potassium methoxide, ethoxide, and tert-butoxide are shown to provide convenient kinetics. See Example 2, Table 1. As in the hydrosilation reactions, the potassium counter ion appears to play a critical, albeit unknown, role in the generation of the active silylating species. As such, in the present context, a description of potassium alkoxide, or any specific potassium alkoxide, should be interpreted as the named chemical entity added as such, or the result of the addition of separate alkoxide potassium cation sources, such that the potassium alkoxide is or may be seen as generated in situ.

While the relative amounts of organodisilane and the alkoxide base is not believed to be particularly important, so long as both are present in sufficient quantities, in certain embodiments, the organodisilane and the at least alkoxide base are present together at a molar ratio, with respect to one another, in a range of from about 20:1 to about 1:1. In other embodiments, these ratios may be on the order of about 5:1 to about 1:1, from about 3:1 to about 1:1, or from about 3:2 to about 1:1. The silylation reactions appear also to favor those conditions where the base is sub-stoichiometric, 0.01:1 to 0.9:1, with respect to the substrate, especially for more active systems. Further embodiments provide that the base is present with respect to the substrate at a ratio of from about 0.01:1 to about 0.6, or from about 0.1:1 to about 0.6.

To this point, the disclosure has been described in terms of the chemical system capable of silylating aromatic compounds or moieties, but it should also be apparent that the invention also includes the methods of carrying out these transformations. That is, various additional embodiments include those methods where an organic substrate comprising a heteroaromatic moiety is contacted with any of the chemical systems described above under conditions sufficient to silylate at least a portion of the substrate. That is, certain embodiments provide methods, each method comprising contacting an organic substrate comprising a heteroaromatic moiety with a mixture of (a) at least one organodisilane and (b) at least one alkoxide base, preferably potassium alkoxide, and more preferably potassium ethoxide or tert-butoxide, under conditions sufficient to silylate the substrate. In preferred embodiments, the systems are preferably, but not necessarily, substantially free of a transition-metal compound. These embodiments are generally done in the liquid phase, without UV irradiation or electric or plasma discharge conditions.

In some embodiments, the conditions sufficient to silylate the organic substrate comprise heating the substrate with a mixture of (a) at least one organodisilane and (b) at least one alkoxide base, preferably potassium alkoxides, and more preferably potassium ethoxides or tert-butoxides, at a temperature in a range of about 10° C. to about 165° C. In some cases, the temperatures may be applied in a range of from about 20° C., about 30° C., about 40° C., about 50° C., or about 60° C., to about 125° C., about 100° C., or to about 80° C. Any of the temperatures described in the Examples may be considered independent embodiments. Typical operating reaction times may range from about 2 hours, from about 4 hours, from about 6 hours, or from about 10 hours to about 28 days, to about 14 days, to about 7 days, to about 4 days, to about 3 days, to about 48 hours, to about 24 hours, to about 12 hours, or to about 6 hours.

As described above, those features described as relevant for the chemical systems for silylating heteroaromatic compounds and heteroaromatic moieties are also relevant for the methods of silylating these heteroaromatic compounds and heteroaromatic moieties. For example, in some embodiments, the methods provide that the system is substantially free of water, oxygen, or both water and oxygen.

In other embodiments, at least one organodisilane comprises an organodisilane of Formula (I):

$$(R)_3Si—Si(R)_3 \quad (I)$$

wherein:

each R is independently H, optionally substituted $C_{1-12}$ alkyl or heteroalkyl, optionally substituted $C_{5-20}$ aryl or $C_{4-20}$ heteroaryl, optionally substituted $C_{6-30}$ alkaryl or $C_{4-30}$ heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or —O—$C_{4-20}$ heteroaryl, optionally substituted —O—$C_{6-30}$ alkaryl or $C_{4-30}$ heteroalkaryl, or optionally substituted —O—$C_{6-30}$ aralkyl or —O—$C_{4-30}$ heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon, In still other embodiments, the organodisilane is $(R)_3Si—Si(R)_3$, where R is independently $C_{1-6}$ alkyl, preferably methyl, ethyl, propyl, tert-butyl, benzyl, aryl or heteroaryl. $(CH_3)_3Si—Si(CH_3)_3$ and $(CH_3CH_2)_3Si—Si(CH_2CH_3)_3$  have been demonstrated to especially work well in the Examples below, though the various embodiments are not limited to these two materials.

In some embodiments, at least one R may be hydrogen, but the situation where at least one R is H not required in the present disclosure. In other embodiments, none of R is hydrogen. One may appreciate that in those circumstances where at least one R is hydrogen there will be internal competition between reaction pathways where the disilane character of the reagent competes with the Si—H character of the reagent under the reaction conditions, especially since alkoxides are shown to mediate both pathways. In such circumstances, the product and product distribution will reflect the outcome of that competition.

The at least one strong base may comprise an alkali metal or alkaline earth alkoxide, as described above, for example, where the at least one alkoxide comprises a $C_{1-12}$ linear or branched alkyl moiety or a $C_{5-10}$ aryl or $C_{4-10}$ heteroaryl moiety, preferably methoxide, ethoxide, propoxide, butoxide, or 2-ethyl-hexyl alkoxide. In most preferred embodiments, the alkoxide is potassium tert-butoxide.

In certain embodiments, the organodisilane and the alkoxide, are present together at a molar ratio, with respect to one another, in a range of from about 20:1 to about 1:1. In certain embodiments alkoxide and organic substrate are present together at a molar ratio, with respect to one another, in a range of from about 0.01:1 to about 5:1. Preferably the alkoxide is sub-stoichiometric—i.e., in a ratio of from about 0.01:1 to about 0.9:1—with respect to the organic substrate. That is, the methods may be considered to be catalytic with respect to the bases contemplated herein.

Additionally, in the context of the methods, the term "substantially free of a transition-metal compound" carries the same connotations and related embodiments as described supra for the chemical system; i.e., reflecting that the methods are effectively conducted in the absence of any deliberately added transition-metal catalyst(s). Noting here that certain embodiments of the chemical system may comprise the at least one organodisilane, and alkoxide, it should be appreciated that independent embodiments provide that the levels of transition metals are maintained below the levels described, when considering each of these mixture combinations.

The methods are fairly flexible with respect to substrates. In representative, non-limiting embodiments, the methods are applied to an organic substrate, monomeric, oligomeric, or polymeric, comprising a heteroaryl moiety. Non-limiting heteroaryl moieties include those an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, dibenzothiophene. In more preferred embodiments, the substrate comprises a moiety comprising an optionally substituted furan, pyrrole, thiophene, pyrazole, imidazole, benzofuran, benzopyrrole, benzothiophene, indole, azaindole dibenzofuran, xanthene, dibenzopyrrole, or dibenzothiophene moiety. Independent embodiments provide that the methods yield silylated products substituted as described herein.

In other specific embodiments, the methods are operable on substrates comprising the following moieties:

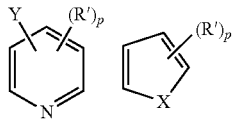

where X is N—R", O, or S;
Y is H, N(R")$_2$, O—R", or S—R"
p is 0 to 4, 0 to 3, 0 to 2, or 0 to 1;
R' is a functional group "Fn," as described above, or (R')$_p$ comprises a fused alicyclic, heteroalicyclic (e.g., methylene, ethylene, or propylene linked diether), aryl or heteroaryl moiety; and
R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Exemplary fused heterocyclic moieties include, for example, the groups:

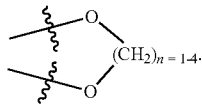

Ethylenedioxothiophene is but one example of such a heteroaryl diether.

In other embodiments, the methods are operable on organic substrates comprising the following moieties:

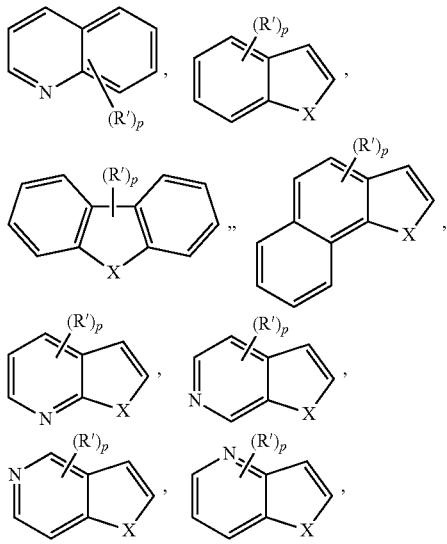

where X, Y, R', R" and p are as defined above. Note that the designation $(R')_p$, in each case, is intended to allow for substitution on either aromatic ring.

Mixed aryl-heteroaryl systems generally preferentially silylate the heteroaryl ring.

While the methods and systems are not limited to the ultimate position of the silylation, in some cases, certain patterns are seen. For example, the silylation reactions with substrates comprising 5-membered heteroaryl moieties also provide remarkably clean and apparently tunable regioselectivities. For example, such substrates can silylate at the C-2 or C-3 position, depending on time and temperature, but tend to favor substitution at the C-2 position under the milder conditions.

Electron-rich systems or electron-donating groups or substituents appear to be generally more reactive than electron-poor systems poor electron-withdrawing groups or substituents. Having said this, the use of the organodisilane reaction systems provides a more facile means of silylating pyridines, representative of electron poor systems, relative to those reactions using hydrosilanes. In the case of pyridines, the present results coupled with results described in U.S. patent application Ser. No. 14/818,417, indicate that silylation at the C-4 position is preferred.

Unless otherwise stated, reference to silylation at a specific position is intended to connote a regioselectivity or regiospecificity of a product at that position of greater than about 80%. But other embodiments provide that the regiospecificity at that position is greater than about 50%, greater than about 75%, greater than about 90%, or greater than about 95%.

As shown in application Ser. No. 14/818,417, silylation reactions using hydrosilane reagents are remarkably tolerant to a range of functional groups, and it is expect that these tolerances extend to the instant system(s). Carbonyl groups in general were not tolerated, but can be made compatible if protected as the corresponding acetal or ketal. Aryl-F, Aryl-Cl, Aryl-CF$_3$, epoxide, N-alkyl aziridine, cis- and trans-olefins, acetylene, pyridine, and tertiary amine and phosphine moieties are all compatible with the silylation chemistry. Even free OH and NH groups are tolerated to some extent, apparently owing to a fortuitous silylative protection of the heteroatom in situ. By contrast, the presence of Aryl-Br, Aryl-I, Aryl-CN, and Aryl-NO$_2$ all appear to shut down the reaction. The present versatility is expected to be present also using organodisilane reagents. This versatility is important for the application of the current method to, for example, alkaloid natural product synthesis and pharmaceutical science applications either at an early stage or for advanced intermediate functionalization.

The products of the inventive methods are useful in a range of agrichemical, pharmaceutical, and electronics applications, as described herein. Heteroarylsilane derivatives, such as described herein, are known to undergo a variety of powerful synthetic transformations; a number of representative examples are demonstrated here. Again, each of these downstream transformations is accessible because of the present inventive processes, and so these downstream steps (when coupled with the inventive silylations) are considered within the scope of the present invention.

The use of aromatic (aryl or heteroaryl) disilanes, such as those described herein, are useful synthons for the preparation of biaryl/biaromatic compounds, for example, using the Hiyama coupling methods generally recognized in the art. As understood by the skilled artisan, the term "biaromatic" refers to two independent aromatic/heteroaromatic ring systems joined by a single bond—e.g., bifuran, biphenyl, bipyridine, bithiophene, phenyl-pyridine, etc. The skilled artisan would be well able to combine the teachings of these Hiyama coupling methods with those presented here, without undue experimentation, to prepare biaryl/biaromatic compounds, and such preparations are considered within the scope of the present invention. Also, Ball and colleagues (Ball et al., Science 28 Sep. 2012: Vol. 337 no. 6102 pp. 1644-1648, which is incorporated by reference herein for its teaching of the catalysts, methods, and substrates) have more recently described another method, using gold catalysts, to couple trialkyl silanes, such as those described herein, to form biaryl/biaromatic compounds. Again, the skilled artisan would be well able to combine the teachings of the Ball coupling, including at least the second aryl compounds taught or suggested in the Ball reference, again without undue experimentation, to prepare biaromatic compounds, and such methods and preparations are considered within the scope of the present invention. In such embodiments, a silylated product of the present invention, whether isolated or generated in situ, is further reacted under conditions (including the presence of a suitable transition metal catalyst) sufficient to couple the silylated product with a second aromatic compound to prepare the biaromatic product. As intended herein, the second aromatic compound comprises an optionally substituted aromatic moiety, including optionally substituted aryl and heteroaryl moieties, where the terms "optionally substituted," "aromatic," "aryl," and "heteroaryl" carry the same definitions as already described herein.

The conversion of heteroaromatic silanes, such as those described herein, are also known to be convertible to heteroaromatic hydroxy compounds, using the well-known Fleming-Tamao oxidation methods. The skilled artisan would be well able to combine the teachings of these Fleming-Tamao oxidations with those presented here, again without undue experimentation, to prepare hydroxylated aromatic compounds, and such methods and preparations are considered within the scope of the present invention. In such embodiments, the aromatic silylated products of the present invention, whether isolated or generated in situ, are further reacted under conditions (including the presence of a suitable transition metal catalyst) sufficient to convert the silylated product to hydroxylated aromatic products. Once hydroxylated, the aromatic products can be converted to the corresponding alkyl or aryl ethers, alkyl or aryl esters, halides (chloro, bromo, fluoro, iodo), nitrates, nitrites, or other similar functional groups by conventional methods. Aryl or heteroaryl iodides are especially convenient precursors for a range of coupling reactions (see, e.g., the palladium/copper-catalyzed sila-Sonogashira reactions of such compounds with alkynylsilanes as described in Nishihara, et al., Tetrahedron Letters, 50 (2009) 4643-4646). All such transformations and products resulting therefrom are considered within the scope of the present invention (when conducted in conjunction with the inventive silylations)

Still further embodiments include those where the heteroaromatic silylated products of the present invention, whether isolated or generated in situ, are further reacted under conditions sufficient (including the presence of a suitable transition metal catalyst) to convert the aromatic silylated product to boronic halides and esters, halides (including chloro, bromo, and iodo), and nitroso groups using the methods described, for example, in Zhao, et al., Organic Letters, 2005, Vol. 7, No. 13, 2523-2526. The skilled artisan would be well able to combine the teachings of these reactions with those presented here, again without undue experimentation, to prepare carboxylated aromatic compounds, and such methods and preparations are considered within the scope of the present invention. Also, as described in the Zhao reference, these aromatic silylated precursors, derived from the instant invention, can also be cross-coupled with aromatic halides using the Suzuki-Miyaura cross-coupling protocols described above, to arrive at biaromatic products.

The demonstrated ability to silylate substituted thiophenes and terthiophenes also provides for further reactions of these products with perfluoroarenes, to provide alternating thiophene-perfluoroarene copolymers, as described in Wang Y. and Watson M., J. Amer. Chem. Soc., 2006, 128, 2536-2537. The skilled artisan would be well able to combine the teachings of Wang and Watson with those presented here, again without undue experimentation, to prepare transition-metal-free alternating thiophene-perfluoroarene copolymers, and such methods and the products derived therefrom are within the scope of the present invention.

Organosilicon has been extensively investigated in the development of advanced materials owing to silicon's unique physical and chemical properties. Within this context, the present disclosure provides examples of compounds and transformations that are valuable in the materials and pharmaceutical context. In but one example, a high-yielding bis-silylation of thiophene monomer furnished the starting material for an entirely transition-metal-free catalytic route to alternating copolymers. Finally, the monoselective silylation of the 3,4-ethylenedioxythiophenemonomer provided a potential strategy for the modification of polythiophene-derived materials. The general ability to silylate thiophenes (including EDOT) is one of the many important aspects of the present invention.

Sila-drug analogues have garnered much attention from medicinal chemists because they can offer improved stability, solubility and pharmacokinetic properties compared with the parent all-carbon compounds. Moreover, the installed organosilicon functionality can serve as a synthetic handle for subsequent elaboration, facilitating library synthesis and enabling structure-activity relationship studies.

The following listing of embodiments is intended to complement, rather than displace or supersede, the previous descriptions.

Embodiment 1

A method comprising contacting an organic substrate comprising a heteroaromatic moiety with a mixture comprising or consisting essentially of (a) at least one organodisilane and (b) at least one strong base, preferably an alkoxide base, more preferably a potassium ethoxide or potassium tert-butoxide base, under conditions sufficient to silylate the substrate.

Embodiment 2

The method of Embodiment 1, wherein the mixture and substrate are substantially free of transition-metal compounds.

Embodiment 3

The method of Embodiment 1 or 2, that is substantially free of water, oxygen, or both water and oxygen.

Embodiment 4

The method of any one of Embodiments 1 to 3, wherein at least one organodisilane comprises an organodisilane of Formula (I):

$$(R)_3Si—Si(R)_3 \quad (I)$$

wherein:

each R is independently optionally substituted H, $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroalkaryl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 5

The method of any one of Embodiments 1 to 4, wherein each R is independently $C_{1-6}$ alkyl, benzyl, or phenyl, preferably $C_{1-6}$ alkyl; i.e., none of R is hydrogen.

Embodiment 6

The method of any one of Embodiments 1 to 4, wherein at least one R is H.

Embodiment 7

The method of any one of Embodiments 1 to 6, wherein the at least one strong base comprises an alkali or alkaline metal alkoxide, preferably an alkali metal alkoxide.

Embodiment 8

The method of any one of Embodiments 1 to 7, wherein the alkali or alkaline metal alkoxide, preferably an alkali metal alkoxide in the presence or associated with a potassium ion.

Embodiment 9

The method of any one of Embodiments 1 to 8, wherein the at least one alkoxide comprises a $C_{1-12}$ linear or branched alkyl moiety or a $C_{5-10}$ aryl or heteroaryl moiety.

Embodiment 11

The method of any one of Embodiments, wherein the at least one alkoxide comprises methoxide, ethoxide, propoxide, butoxide, or 2-ethyl-hexyl alkoxide.

Embodiment 12

The method of any one of Embodiments 7 to 11, wherein the alkali or alkaline metal alkoxide is a potassium. The potassium alkoxide may be added as such or generated in situ from separate sources of alkoxide anions and potassium cations.

Embodiment 13

The method of any one of Embodiments 1 to 12, where the organodisilane is hexamethyldisilane or hexa-ethyldisilane and the strong base is potassium methoxide, potassium ethoxide, or potassium tert-butoxide, preferably K-t-OBu.

Embodiment 14

The method of any one of Embodiments 1 to 13, wherein the organodisilane and the at least one strong base are present together at a molar ratio, with respect to one another, in a range of from about 20:1 to about 1:1, preferably or conveniently 10:1.

Embodiment 15

The method of any one of Embodiments 1 to 14, wherein the at least one strong base and substrate are present together at a molar ratio, with respect to one another, in a range of from about 0.01:1 to about 0.9:1, preferably or conveniently 0.2:1.

Embodiment 16

The method of any one of Embodiments 1 to 15, wherein the substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, pyridine, or a dibenzothiophene.

Embodiment 17

The method of any one of Embodiments 1 to 16, wherein the organic aromatic substrate comprises at least one of the following moieties:

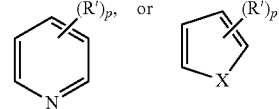

where X is N—R″, O, or S;
Y is H, N(R″)$_2$, O—R″, or S—R″
p is 0 to 4;

R' is a halo, hydroxyl, sulfhydryl, alkoxy, aryloxy, aralkyloxy, alkaryloxy, acyl, acyloxy), alkoxycarbonyl, aryloxycarbonyl, halocarbonyl, alkylcarbonato, arylcarbonato, carboxylato (—COO—), dialkyl-substituted carbamoyl, di-haloalkyl-substituted carbamoyl, di aryl-substituted carbamoyl, di-alkyl-substituted thiocarbamoyl, di-aryl-substituted thiocarbamoyl, di-N-alkyl),N-aryl-substituted thiocarbamoyl, cyano, cyanato, thiocyanato, di-alkyl-substituted amino, di-aryl-substituted amino, arylimino (—CR═N (aryl), where R=alkyl, aryl, alkaryl, aralkyl), nitro, nitroso, alkylsulfanyl, arylsulfanyl, alkylsulfinyl, arylsulfinyl, alkylsulfonyl, boronato (—B(OR)$_2$ where R is alkyl or other hydrocarbyl); or (R')$_p$ comprises an optionally substituted fused alicyclic, heteroalicyclic heteroalicyclic (e.g., methylene, ethylene, or propylene linked diether), aryl or heteroaryl moiety; and R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Embodiment 18

The method of any one of Embodiments 1 to 20, wherein the substrate comprises at least one of the following moieties:

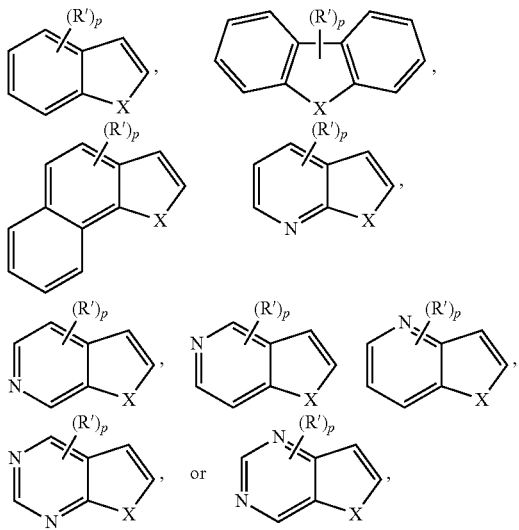

where X is N—R", O, or S;
Y is H, N(R")$_2$, O—R", or S—R"
p is 0 to 4;
R' is a halo, hydroxyl, sulfhydryl, alkoxy, aryloxy, aralkyloxy, alkaryloxy, acyl, acyloxy), alkoxycarbonyl, aryloxycarbonyl, halocarbonyl, alkylcarbonato, arylcarbonato, carboxylato (—COO—), dialkyl-substituted carbamoyl, di haloalkyl-substituted carbamoyl, di aryl-substituted carbamoyl, di-alkyl-substituted thiocarbamoyl, di-aryl-substituted thiocarbamoyl, di-N-alkyl),N-aryl-substituted thiocarbamoyl, cyano, cyanato, thiocyanato, di-alkyl-substituted amino, di-aryl-substituted amino, arylimino (—CR═N(aryl), where R=alkyl, aryl, alkaryl, aralkyl), nitro, nitroso, alkylsulfanyl, arylsulfanyl, alkylsulfinyl, arylsulfinyl, alkylsulfonyl, boronato (—B(OR)$_2$ where R is alkyl or other hydrocarbyl); or (R')$_p$ comprises an optionally substituted fused alicyclic, heteroalicyclic heteroalicyclic (e.g., methylene, ethylene, or propylene linked diether), aryl or heteroaryl moiety; and R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Embodiment 19

The method of any one of Embodiments 1 to 18, wherein the organic substrate comprises a heteroaryl moiety of structure:

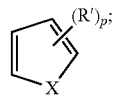

in some of these embodiments, the silylation occurs at the C-2 or C-3 position of the heteroaryl ring.

Embodiment 20

The method of any one of Embodiments 1 to 19, wherein the organic substrate comprises a heteroaryl moiety of structure:

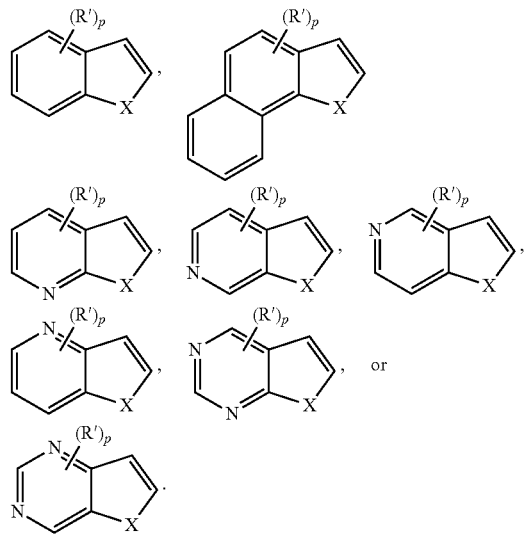

In some subsets of this Embodiment, the silylation occurs at the C-2 or C-3 position of the 5-membered heteroaryl ring.

Embodiment 21

The method of any one of Embodiments 1 to 20, wherein the aromatic substrate is polymeric, oligomeric, or a polymeric precursor.

Embodiment 22

The method of any one of Embodiments 1 to 21, wherein the aromatic silylated product is further reacted under conditions sufficient to couple the silylated product with a second aromatic compound to form a biaromatic product.

Embodiment 23

The method of any one of Embodiments 1 to 21, wherein the aromatic silylated product is further reacted under conditions sufficient to convert the silylated product to a hydroxylated (protected or free hydroxyl), alkoxylated (or aryloxylated), or alkyl or aryl carboxylated product.

Embodiment 24

The method of any one of Embodiments 1 to 21, wherein the aromatic silylated product is further reacted under conditions sufficient to convert the silylated product to an aromatic alpha-olefin product.

Embodiment 25

The method of any one of Embodiments 1 to 21, wherein the aromatic silylated product is further reacted under conditions sufficient to convert the silylated product to an aromatic halide (chloro, bromo, fluoro, iodo), nitrate, or nitrite.

Embodiment 26

The method of any one of Embodiments 1 to 21, wherein the aromatic silylated product is further reacted under conditions sufficient to convert the silylated product to an aromatic boronic halide or boronic ester.

Embodiment 27

The method of any one of Embodiments 1 to 21, where X is S, wherein the silylated product is a silylated thiophene product and the silylated thiophene product is further reacted under conditions sufficient to convert the silylated product to an alternating thiophene-perfluoroarene copolymer.

Embodiment 28

A chemical system for silylating aromatic substrates comprising a heteroaromatic moiety, said system comprising or consisting essentially of a mixture of (a) at least one organodisilane and (b) at least one strong base, preferably an alkoxide base, more preferably a potassium ethoxide or potassium tert-butoxide base, the system in the presence of a heteroaromatic substrate being capable of silylating the heteroaromatic substrate.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1

General Information

Unless otherwise specified, the methods and materials used in these Examples are the same as or comparable to the methods described in U.S. patent application Ser. Nos. 14/043,917, 14/043,929, and/or 14/818,417, the contents of which is incorporated herein by reference in their entirety, and the interested reader is referred there for the descriptions. The representative organodisilanes, hexamethyldisilane (sometimes described herein as "Me$_3$Si—SiMe$_3$" or "TMS-TMS" or "TMS$_2$") and hexaethyldisilane (sometimes described herein as "TES-TES" or "TES$_2$") were obtained from Sigma-Aldrich and used as received. The Examples described herein were all carried out under nitrogen atmosphere. Products were isolated using silica gel chromatography.

Example 2

Evaluation of Basic Activators

N-methyl indole is shown to act as an excellent exemplar of the reactivities associated with this inventive chemistry, consistent with studies using hydrosilane reagents (see, e,g, U.S. patent application Ser. No. 14/043,917). The effects of various bases were evaluated under the following nominal conditions, with the results provided in Table 1:

TABLE 1

Evaluation of Basic Activators for N-Methyl Indole System.

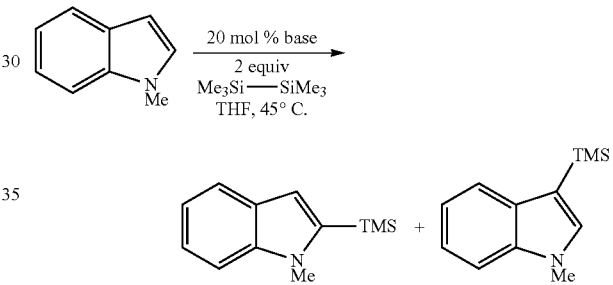

| Entry | Base | Conversion (%) | C2:C3 |
|---|---|---|---|
| 1 | KOt-Bu | 79 | 4:1 |
| 2 | KOH | 0 | — |
| 3 | KOEt | 78 | 5.6:1 |
| 4 | KOMe | 20 | >20:1 |
| 5 | KOTMS [a] | 1 | — |
| 6 | KHMDS [b] | 0 | — |
| 7 | KH | 0 | — |
| 8 | NaO—t-Bu | 0 | — |
| 9 | LiO—t-Bu | 0 | — |
| 10 | Mg(O—t-Bu)$_2$ | 0 | — |
| 11 | Ca(O—i-Pr)$_2$ | 0 | — |
| 12 | BaO—t-Bu)$_2$ | 0 | — |

The reactions were run with 0.2 mmol of N-Methylindole, 0.4 mmol of Me$_3$Si—SiMe$_3$ in 0.2 mL THF at 45° C. for 68 hours
[a] KOTMS is potassium trimethylsilanolate
[b] KHMDS is Potassium bis(trimethylsilyl)amide or Potassium(K) HexaMethylDiSilazide Previous results using hydrosilane silylating agents (see U.S. patent application Ser. No. 14/043,917), showed that KOH was operable under comparable conditions (3 equiv. Et$_3$SiH with N-methyl indole substrates at 65° C. in THF), and provided convenient and useful yields (ca. 85% yield of the C-2 silylated product. By contrast, in the present systems, using KOH and disilane reagents, even up to 100° C. provide low yields of complicated product mixtures. Similarly, the absence of reactivity here using KOTMS and KHMDS, contrasts their ability to facilitate silylations using hydrosilanes (again, see U.S. patent application Ser. No. 14/043,917).

Example 3

Evaluation of Solvent

The effects of various bases were evaluated under the following nominal conditions, with the results provided in Table 2:

TABLE 2

Evaluation of Solvent for N-Methyl Indole System.

| Entry | Solvent | Conversion (%) | C2:C3 |
|---|---|---|---|
| 1 | Tetrahydrofuran | 82 | 7.4:1 |
| 2 | 1,4 dioxane | 7 | — |
| 3 | Dimethyl ether | 35 | 66:1 |
| 4 | Methyl-tert-butyl ether | 0 | — |
| 5 | dichloromethane | 0 | — |
| 6 | Toluene | 0 | — |
| 7 | Acetonitile | 0 | — |
| 8 | HMPA [a] | 36 | 26.1 |
| 9 | Neat | 0 | — |
| 10 | Neat (with KO—t-Bu) | 0 | — |

The reactions were run with 0.2 mmol of N-Methylindole, 0.4 mmol of Me$_3$Si—SiMe$_3$ in 0.2 mL THF at 45° C. for 68 hours
[a] HMPA is HexaMethylphosphoramide These results show a clear preference, if not a requirement, for the presence of solvents having an oxygen donor group (e.g., ethers, especially non-tertiary ethers, alkylphosphoramides including HMPA, DME, THF, 2-methyl-THF, dioxanes), at least under these relatively mild conditions. Surprisingly, these present results show the poor utility of methyl-tert-butyl ether (MTBE) in these organodisilane reactions, given its utility with comparable hydrosilane systems (see, e.g., Table 1 of U.S. patent application Ser. No. 14/043,917).

Example 4

Evaluation of Organodisilane Equivalents

The effects of various base ratios were evaluated under the following nominal conditions, with the results provided in Table 3:

TABLE 3

Evaluation of Organodisilane Equivalents for N-Methyl Indole System.

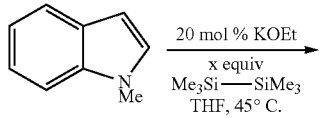

TABLE 3-continued

| Entry | X equivalent | Conversion (%) | C2:C3 |
|---|---|---|---|
| 1 | 0.6 | 35 | 22:1 |
| 2 | 1.1 | 45 | 22:1 |
| 3 | 1.5 | 79 | 8.1:1 |
| 4 | 2.0 | 78 | 8.4:1 |
| 5 | 3.0 | 83 | 14:1 |

The reactions were run with 0.2 mmol of N-Methylindole, 0.4 mmol of Me$_3$Si—SiMe$_3$ in 0.2 mL THF 45° C. for 68 hours

Example 5

Reproducibility of Systems

Figure 2:
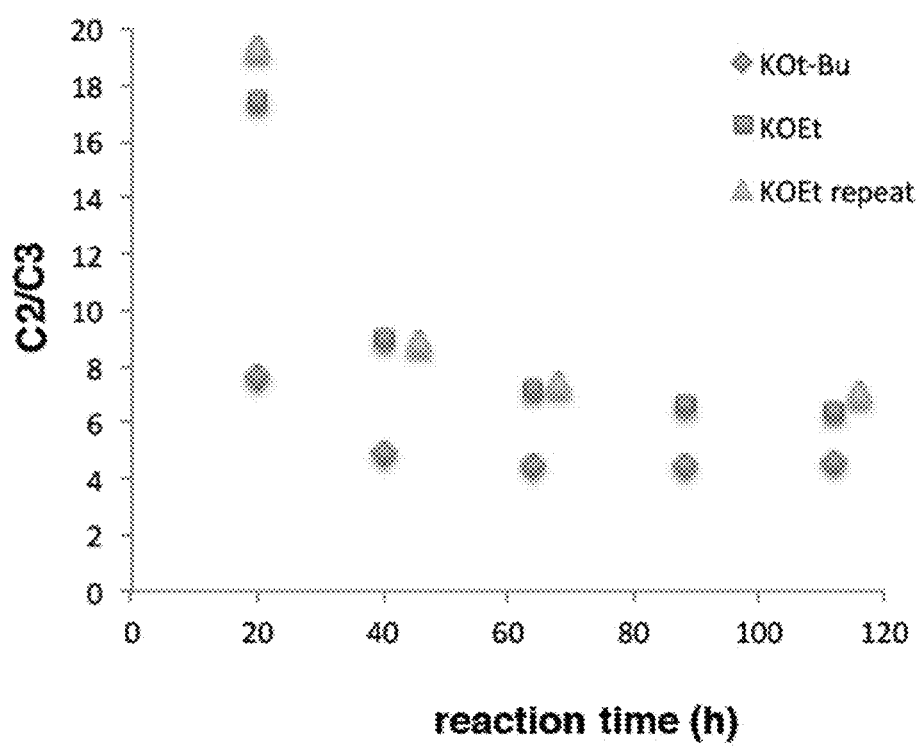
FIG. 2 presents data showing the C2:C4 selectivity as a function of reaction time for some of the inventive systems.

Studies were conducted to evaluate the reproducibility of the reactions of two representative base systems (potassium ethoxide and potassium tert-butoxide) using N-methyl indole as a substrate. The first two reactions (KOtBu and KOEt) were run at 0.2 mmol N-Me-indole, 0.4 mmol hexamethyldisilane, 0.2 mL THF, 0.04 mmol base (KOtBu or KOEt) at 45° C. in a N$_2$ filled glove box. Aliquots were taken with a glass capillary tube and transferred out of the glovebox to be analyzed by GC. The repeat reaction was run at 0.5 mmol scale with the same ratio of catalyst, reagents, and concentration under the same conditions. The results are shown in FIG. 1 (conversion percentage) and FIG. 2 (C2:C3 ratio).

Example 6

Evaluation of Selected Precursors

Example 6.1

Experimental Condition A

Where described as done according to "Condition A," the reactions were conducted using potassium ethoxide (KOEt) according to:

1 equivalent substrate:20 mol % KOEt:2 equivalent hexamethyldisilane (TMS$_2$) at a concentration of 1M substrate in THF (tetrahydrofuran) at 45° C. for 24 hours

Example 6.2

Experimental Condition B

Where described as done according to "Condition B," the reactions were conducted using potassium tert-butoxide (KO-t-Bu) according to:

1 equivalent substrate:20 mol % KO-t-Bu:2 equivalent hexamethyldisilane (TMS$_2$) at a concentration of 1M substrate in THF (tetrahydrofuran) at 45° C. for 24 hours

Example 6.3

Silylation of N-Methyl Indole

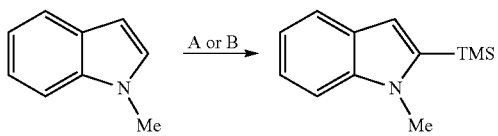 [SMILES: Cn1ccc2ccccc21 ; "A or B" ; Cn1c([Si](C)(C)C)cc2ccccc21]

In addition to the experiments with N-methyl indole described above, additional experiments were conducted using experimental Condition A and Condition B. Both conditions resulted in comparable isolated yields (57% for Condition A and 59% for Condition B), though Condition A yielded a higher C2:C3 ratio (15.2:1, determined by gas chromatography, average of two runs) than did Condition B 8.75:1). The products were characterized by NMR and Mass Spectrometry: [M+H]+ Calcd. 204.1203. Found 204.1196. $^1$H NMR (300 MHz, CDCl$_3$), δ: 7.61 (dt, J=7.9, 0.9 Hz, 1H), 7.32 (m, 1H), 7.22 (m, 1H), 7.08 (m, 1H), 6.69 (m, 1H), 3.86 (s, 3H), 0.39 (s, 9H).

The activity of these organodisilane reagents with potassium alkoxides with N-methyl indole is comparable both in terms of kinetics and product selectivity (site of silylations) to systems using hydrosilane reagents. Such comparable reactivity with these synthetically important heteroaromatic frameworks provides support for the utility of the present methods with the breadth of substrates previously demonstrated, as well as their benzofuran and benzothiophene cousins. That is, the facile and selective reactions between systems comprising various hydrosilanes/KO-t-Bu and substituted or unsubstituted benzofurans, substituted or unsubstituted benzothiophene, substituted or unsubstituted N-aryl or alkyl indoles (e.g., N-butyl indole, N-ethyl indole, N-methyl indole, N-methoxymethyl indole, N-phenyl indole, 1-((2-(trimethylsilyl)ethoxy)methyl)-1H-indole, 4-methyl-N-methyl indole, 1,3-dimethyl-1H-indole, 5-methyl-N-methyl indole, 6-alkyl methyl-N-methyl indole, 7-methyl-N-methyl indole, N-methyl-5-methoxyindole, 5-(benzyloxy)-1-methyl-indole, 5-(methoxymethyl)-N-methyl indole), substituted or unsubstituted furo-pyridines, substituted or unsubstituted thienopyridines, substituted or unsubstituted pyrrolo-pyridines (e.g., 1-Methyl-1H-pyrrolo[3,2-b]pyridine, 1-Methyl-1H-pyrrolo[3,2-c]pyridine, 1-Methyl-1H-pyrrolo[2,3-b]pyridine, 1-Benzyl-1H-pyrrolo[2,3-b]pyridine under comparable reaction conditions gives enabling support that the present systems are operable on the same range of substrates.

Example 6.4

Silylation of Thiophene

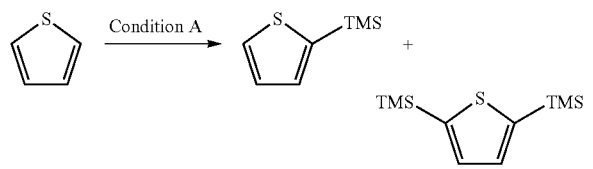

Experiments conducted with thiophene under Condition A, resulted in a 1:4 ratio of mono:bis silylated product, in 70% combined yield, as determined by 1H NMR. $^1$H NMR for mono (300 MHz, CDCl$_3$), δ: 7.59 (m, 1H), 7.29-7.24 (m, 1H), 7.19 (dd, J=4.6, 3.3 Hz, 1H), 0.34 (s, 9H). $^1$H NMR for bis (300 MHz, CDCl$_3$), δ: 7.34 (s, 2H), 0.34 (s, 18H).

Again, this reactivity (both in terms of kinetics and preference for C-2 silylation site) was comparable to that previously demonstrated for the reaction between thiophene and Et$_3$SiH, as shown in U.S. patent application Ser. No. 14/043,917, giving enabling support that the similar range of substituted and unsubstituted thiophenes are operable with the present methods. This would include, for example, the ability to use the present systems and methods various aryl, heteroaryl, alkyl, and alkoxy substituted thiophenes. The present organodisilane system would be operable on such substrates as exemplified as 2,2':5'2"-terthiophene and EDOT (2,3-dihydrothieno[3,4-b][1,4]dioxine): Exemplary non-limiting examples would include the following transformations, using the present disilane system:

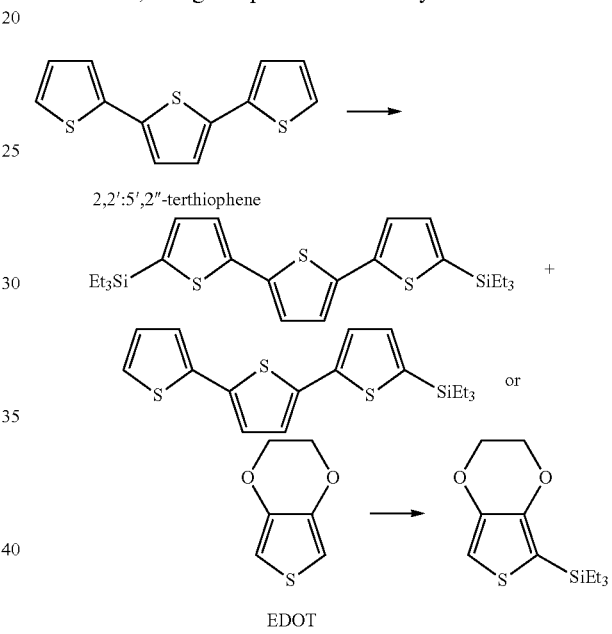

Similarly, the comparable reaction profiles would provide enabling support for aryl, heteroaryl, and alkyl substituted thiophene, as exemplified by such substrates as 2-thiophen-2-yl)pyridine or 2-pentyl thiophene. Exemplary non-limiting examples would include the following transformations, using the present disilane system:

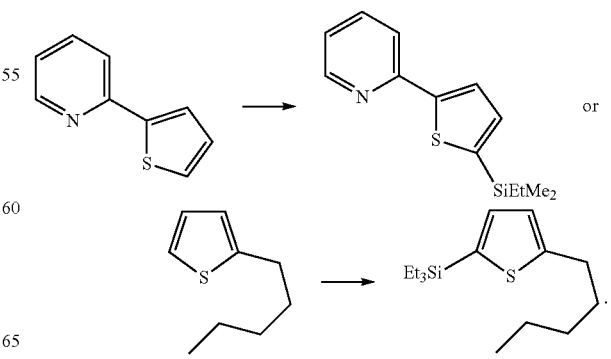

Example 6.5

Silylation of Furan

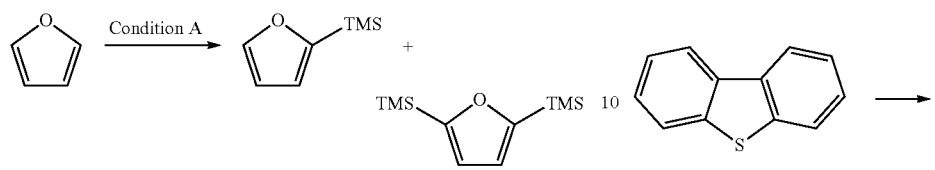

Experiments conducted with furan under Condition A, resulted in a 2:1 ratio of mono:bis silylated product. $^1$H NMR for mono-silylated product (300 MHz, CDCl$_3$), δ: 7.65 (dd, J=1.6, 0.6 Hz, 1H), 6.62 (dd, J=3.2, 0.6 Hz, 1H), 6.38 (dd, J=3.2, 1.7 Hz, 1H), 0.26 (s, 9H). $^1$H NMR for bis-silylated product (300 MHz, CDCl$_3$), δ: 6.60 (s, 2H), 0.26 (s, 18H).

This reactivity (both in terms of approximate kinetics and preference for C-2 silylation site) was comparable to that previously demonstrated for the reaction between furans and alkyl-substituted furans, as shown in U.S. patent application Ser. No. 14/043,917, for example:

This provides enabling support for the ability of the present organodisilane systems to silylate substituted and unsubstituted furans.

Example 6.7

Silylation of Dibenzofuran

Experiments conducted with dibenzofuran under Condition A, at 80° C., resulted in a 1:1 ratio of mono:bis silylated product. Products were identified by NMR using comparison with authentic samples, as described in U.S. patent application Ser. Nos. 14/043,917, 14/043,929, and 14/818,417. The reactivity seen in this example is comparable to that reported in U.S. patent application Ser. No. 14/043,917 for the same substrate. It would be expected, then, that other substrates having this framework (including substituted versions thereof, including for example 4-methoxydibenzo[b,d]furan), or closely related frameworks (e.g., dibenzothiophene) would respond to the present inventive systems and methods in the same way, e.g.,

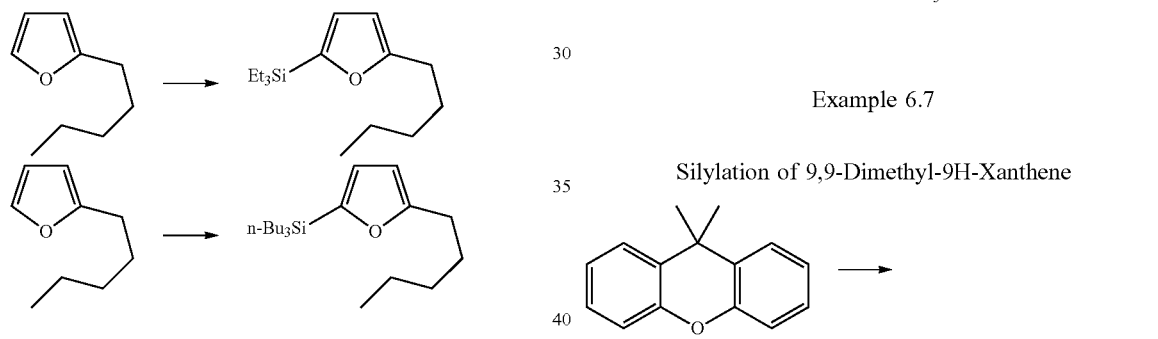

Example 6.7

Silylation of 9,9-Dimethyl-9H-Xanthene

Experiments conducted with 9,9-dimethyl-9H-xanthene under Condition A, at 80° C., resulted only in mono silylated product in 54% (14% RSM) isolated. Products were identified by NMR using comparison with authentic samples. $^1$H NMR (400 MHz, CDCl$_3$), δ: 7.44 (m, 2H), 7.31 (dd, J=7.1, 1.6 Hz, 1H), 7.21 (m, 1H), 7.08 (m, 3H), 1.64 (s, 6H), 0.38 (s, 9H).

Example 6.8

Silylation of 2,6-Di-tert-Butyl-Pyridine

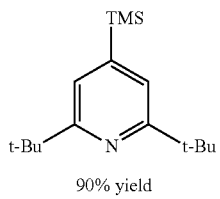

90% yield

In a nitrogen-filled glovebox, KO-t-Bu (11.2 mg, 0.1 mmol, 20 mol %), 2,6-di-tert-butylpyridine (95.5 mg, 0.5 mmol, 1 equiv), THF (0.5 mL, and hexamethyldisilane (146 mg, 1.0 mmol, 2 equiv) were added to a 1 dram vial. The mixture was stirred under nitrogen at 65° C. for 72 hours, removed from the glovebox, and quenched with diethyl ether. The solvents were removed and the crude mixture was purified by silica gel chromatography (5 vol % CH$_2$Cl$_2$ in hexanes): $^1$H NMR (500 MHz, CDCl$_3$), δ 7.22 (s, 2H), 1.39 (s, 18H), 0.31 (s, 9H). $^{13}$C NMR (126 MHz, CDCl$_3$), δ: 166.3, 149.5, 119.5, 37.8, 30.4, −1.3. IR (neat film, NaCl) 2955, 2901, 2866, 1586, 1574, 1536, 1477, 1457, 1389, 1359, 1262, 1250, 1161, 1050, 873, 835 cm$^{-1}$. HRMS (MM:ESI-APCI+) calc'd for C$_{16}$H$_{30}$SiN [M+H]+: 264.2142. found 264.2137.

Note that this facile silylation of pyridine contrasts previous attempts to silylate pyridine substrates using hydrosilanes, even those having electron donating substituents such as methoxy, where comparable reaction conditions resulted in variably low (<15%) yields. For example, U.S. patent application Ser. No. 14/043,917 describes the low and irreproducible yields of the reactions between K—O-t-butoxide and Et$_3$SiH with pyridine itself. Reactions with 2,6-dimethoxy pyridine under comparable conditions showed a mixture of unidentifiable products, and reactions with 2,6-dimethyl pyridine (lutidine) showed preferential silylation of the alpha methyl group. The facile silylation of pyridine or substituted precursors into the C-4 (or para) position using organodisilane reagents suggests an aspect of the reaction mechanism previously not recognized and still not understood, but clearly expands the toolkit for silylating these electron poor substrates.

Example 6.9

Miscellaneous Experiments

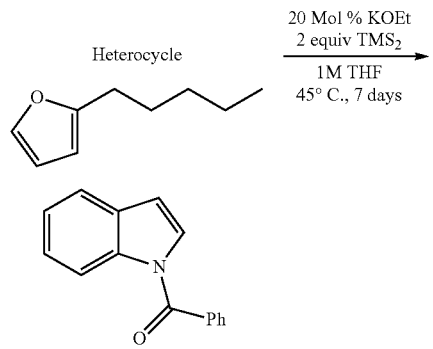

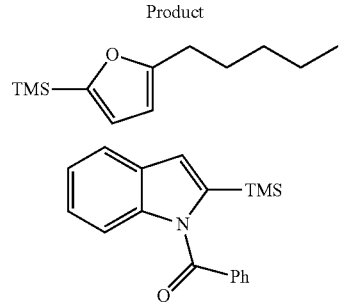

Example 7

Transformations of the Prepared Silanes

Example 7.1

One-Pot Si-Directed Ipso-Substitution/Suzuki-Miyaura Cross-Coupling

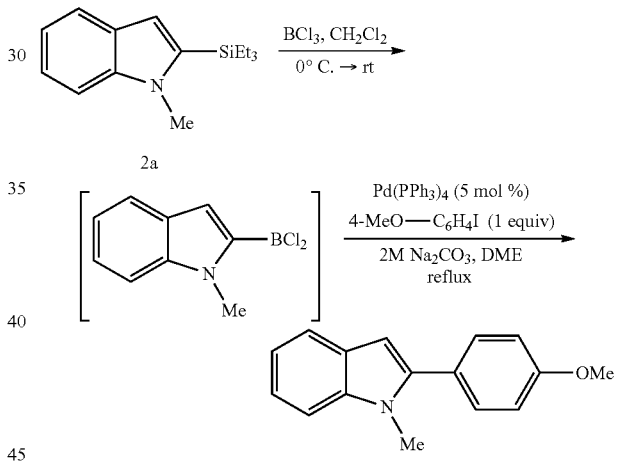

A solution of BCl$_3$ (1.0 M, 0.48 mL, 0.48 mmol) in CH$_2$Cl$_2$ was added by syringe under N$_2$ to a stirred solution of indolesilane 2a (98.2 mg, 0.4 mmol) in CH$_2$Cl$_2$ (4 mL) at 0° C. The mixture was stirred at room temperature for 3 h, after which time the solvent was removed in vacuo. After the residue was dried under high vacuum for 20 min, 4-iodo-anisole (94.0 mg, 0.4 mmol), Pd(PPh$_3$)$_4$ (23.2 mg, 5 mol %), DME (4 mL, degassed) and 2M Na$_2$CO$_3$ aqueous solution (1 mL, degassed) were added and the mixture was stirred under reflux for 5 h. Then the reaction mixture was cooled to room temperature and water (20 mL) was added. The mixture was extracted with Et$_2$O (3×30 mL), the combined organic extracts were washed with brine, dried over Na$_2$SO$_4$ and concentrated. The desired 2-(4-methoxyphenyl)-1-methyl-1H-indole 5 (71.9 mg, 76% yield) was obtained as a white solid after purification by silica gel flash chromatography (gradient elution, 10→33% CH$_2$Cl$_2$ in hexanes). Rf=0.4 (10% EtOAc in hexanes); $^1$H NMR (500 MHz, CDCl$_3$) δ 7.63 (d, J=7.7 Hz, 1H), 7.49-7.39 (m, 2H), 7.36 (d, J=8.2 Hz, 1H), 7.24 (dt, J=8.2, 1.2 Hz, 1H), 7.14 (dt, J=7.9, 1.0 Hz, 1H), 7.05-6.96 (m, 2H), 6.51 (br s, 1H), 3.88 (s, 3H), 3.73 (s, 3H).

Example 7.2

Direct C7 Lithiation-Borylation by a Si-Blocking Group Strategy

This general transformation (i.e., the protection/deprotection of the C2 position in benzofurans, indoles, and thiophenes, including the C7 lithiation-borylation of these silylated derivatives) is considered within the scope of the present invention.

Example 7.2.1

Triethyl(7-(4,4,5,5-tetramethyl-1,3,2-dioxaborolan-2-yl)benzo[b]thiophen-2-yl)silane 7

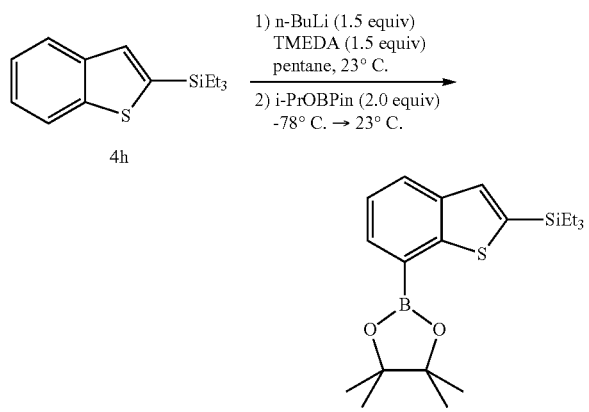

To a flame-dried, round bottom flask charged with a stir bar, capped with a septum and under a steady stream of argon was added benzo[b]thiophen-2-yltriethylsilane 4h (992 mg, 4.0 mmol, 1 equiv), pentane (5.0 mL) and TMEDA (0.703 g, 0.907 mL, 1.5 equiv) at 23° C. n-Butyllithium (1.6 M in hexanes, 3.78 mL, 1.5 equiv) was added dropwise such that the internal temperature remained between 22 and 25° C. (a thermocouple was inserted through the septum directly into the solution for internal monitoring of the temperature). The resultant dark brown solution was allowed to stir at 22° C. for 20 h. The solution was then cooled to −78° C. (dry ice/acetone) and i-PrOBPin (1.52 g, 1.64 mL, 8.06 mmol, 2.0 equiv) was added as a 1 M solution in THF (8.06 mL) dropwise such that the temperature was kept below −75° C. (careful temperature control is crucial for reproducibility). The resulting solution was allowed to stir for 1 h at −78° C. after which time the cooling bath was removed. The solution was allowed to naturally warm to 23° C. and stirred at that temperature for an additional hour. The resulting turbid yellow reaction mixture was carefully quenched with NH$_4$Cl (5 mL). The mixture was extracted with Et$_2$O (3×10 mL), the combined organic fractions were washed with brine, dried over MgSO$_4$, filtered, and the solvent was evaporated to give a viscous brown liquid. The desired product 7 (926 mg, 64% yield) was obtained as a colorless solid after purification by silica gel flash chromatography (gradient elution 0→3% EtOAc in hexanes). Rf=0.2 (100% hexanes); $^1$H NMR (500 MHz, CDCl$_3$) δ 7.91 (dd, J=8.0, 1.3 Hz, 1H), 7.80 (dd, J=7.0, 1.3 Hz, 1H), 7.48 (s, 1H), 7.35 (dd, J=7.9, 7.0 Hz, 1H), 1.42 (s, 12H), 1.10-1.00 (m, 9H), 0.89 (m, 6H); $^{13}$C NMR (125 MHz, CDCl$_3$) δ 149.7, 140.8, 139.8, 132.0, 131.4, 126.4, 123.4, 84.3, 25.1, 7.6, 4.4. IR (Neat Film, NaCl) 2955, 2937, 1375, 1367, 1359, 1134, 1059, 854, 735 cm$^{-1}$; HRMS (EI+) calc'd for C$_{20}$H$_{31}$BSSiO$_2$ [M•+]: 374.1907. found 374.1907.

Example 7.2.2

2-(Benzo[b]thiophen-7-yl)-4,4,5,5-tetramethyl-1,3,2-dioxaborolane 8

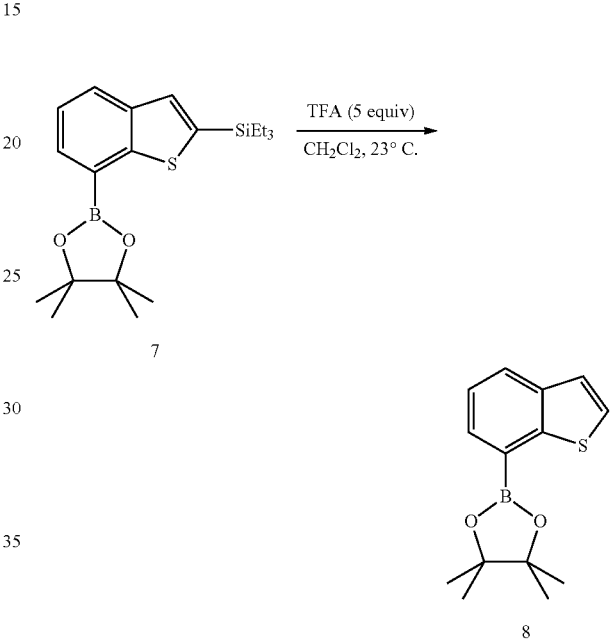

To a vial charged with a magnetic stir bar and triethyl(7-(4,4,5,5-tetramethyl-1,3,2-dioxaborolan-2-yl)benzo[b]thiophen-2-yl)silane 7 (300 mg, 0.80 mmol) was added CH$_2$Cl$_2$ (0.3 mL) and trifluoroacetic acid (306 μL, 4.0 mmol, 5.0 equiv) at room temperature. The reaction was allowed to stir for 3 hours, after which time the mixture was quenched with water (0.5 mL), extracted with Et$_2$O (3×5 mL) and the combined organic fractions were washed with brine (5 mL). The solvents were removed to give 8 (203.8 mg, 98%) as a white solid without further purification. Rf=0.4 (3% EtOAc in hexanes); $^1$H NMR (500 MHz, CDCl$_3$) δ 7.92 (dd, J=7.9, 1.3 Hz, 1H), 7.83 (dd, J=7.1, 1.3 Hz, 1H), 7.48 (d, J=5.5 Hz, 1H), 7.38 (dd, J=7.9, 7.0 Hz, 1H), 7.34 (d, J=5.5 Hz, 1H), 1.41 (s, 12H); $^{13}$C NMR (125 MHz, CDCl$_3$) δ 145.8, 139.4, 132.0, 127.5, 126.7, 123.7, 123.4, 84.4, 25.1. IR (Neat Film, NaCl) 2977, 1564, 1504, 1461, 1372, 1330, 1300, 1267, 1199, 1165, 1135, 1097, 1038, 969, 851, 829, 801, 714, 672 cm$^{-1}$; HRMS (EI+) calc'd for C$_{14}$H$_{17}$BSO$_2$ [M•+]: 260.1042. found 260.1039.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

Each patent, patent application, and publication cited or described in this document is hereby incorporated herein by reference, each in its entirety, for all purposes.

What is claimed:

1. A method comprising contacting an organic substrate having a heteroaromatic moiety with a mixture comprising (a) at least one organodisilane and (b) at least one potassium alkoxide base, in the presence of an organic solvent having an oxygen donor group, under conditions sufficient to silylate the substrate, the method resulting in a heteroaromatic silylated product.

2. The method of claim 1, wherein the mixture and organic substrate are substantially free of transition-metal compounds.

3. The method of claim 1, wherein at least one organodisilane comprises an organodisilane of Formula (I):

$$(R)_3Si-Si(R)_3 \quad (I)$$

wherein:
each R is independently H, optionally substituted $C_{1-12}$ alkyl or $C_{1-12}$ heteroalkyl, optionally substituted $C_{6-20}$ aryl or $C_{5-20}$ heteroaryl, optionally substituted $C_{7-30}$ alkaryl or $C_{6-30}$ heteroalkaryl, optionally substituted $C_{7-30}$ aralkyl or $C_{6-30}$ heteroaralkyl, optionally substituted —O—$C_{1-12}$ alkyl or —O—$C_{1-12}$ heteroalkyl, optionally substituted —O—$C_{6-20}$ aryl or —O—$C_{5-20}$ heteroaryl, optionally substituted —O—$C_{7-30}$ alkaryl or —O—$C_{6-30}$ heteroalkaryl, or optionally substituted —O—$C_{7-30}$ aralkyl or —O—$C_{6-30}$ heteroaralkyl, and, if substituted, the substituents are phosphonato, phosphoryl, phosphanyl, phosphino, sulfonato, $C_1$-$C_{20}$ alkylsulfanyl, $C_6$-$C_{20}$ arylsulfanyl, $C_1$-$C_{20}$ alkylsulfonyl, $C_6$-$C_{20}$ arylsulfonyl, $C_1$-$C_{20}$ alkylsulfinyl, $C_6$-$C_{20}$ arylsulfinyl, sulfonamido, amino, amido, imino, nitro, nitroso, hydroxyl, $C_1$-$C_{20}$ alkoxy, $C_6$-$C_{20}$ aryloxy, $C_2$-$C_{20}$ alkoxycarbonyl, $C_6$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, or where the substituents optionally provide a tether to an insoluble or sparingly soluble support media comprising alumina, silica, or carbon.

4. The method of claim 3, wherein each R is independently $C_{1-6}$ alkyl.

5. The method of claim 3, wherein at least one R is H.

6. The method of claim 1, wherein the at least one potassium alkoxide base comprises a $C_{1-12}$ linear or branched alkyl moiety or a $C_6$-$C_{20}$ aryl or a $C_{5-10}$ heteroaryl moiety.

7. The method of claim 1, wherein the at least one potassium alkoxide base comprises potassium methoxide, potassium ethoxide, potassium propoxide, potassium butoxide, or potassium 2-ethyl-hexyl alkoxide.

8. The method of claim 1, where the organodisilane is hexamethyldisilane or hexa-ethyldisilane and at least one potassium alkoxide base is potassium methoxide, potassium ethoxide, or potassium tert-butoxide.

9. The method of claim 1, wherein the organodisilane and the at least one potassium alkoxide base are present together at a molar ratio, with respect to one another, in a range of from about 20:1 to about 1:1.

10. The method of claim 1, wherein the at least one potassium alkoxide base and the organic substrate are present together at a molar ratio, with respect to one another, in a range of from about 0.01:1 to about 0.9:1.

11. The method of claim 1, wherein the organic substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, pyridine, or a dibenzothiophene.

12. The method of claim 1, wherein the organic substrate comprises at least one of the following moieties:

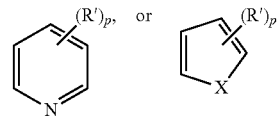

where X is N—R'', O, or S;
p is 0, 1, 2, or 3;
R' is a halo, hydroxyl, sulfhydryl, alkoxy, aryloxy, aralkyloxy, alkaryloxy, acyl, acyloxy, alkoxycarbonyl, aryloxycarbonyl, halocarbonyl, alkylcarbonato, arylcarbonato, carboxylato (—COO—), dialkyl-substituted carbamoyl, di-haloalkyl-substituted carbamoyl, di aryl-substituted carbamoyl, di-alkyl-substituted thiocarbamoyl, di-aryl-substituted thiocarbamoyl, di-N-alkyl,N-aryl-substituted thiocarbamoyl, cyano, cyanato, thiocyanato, di-alkyl-substituted amino, di-aryl-substituted amino, arylimino (—CR=N(aryl), where R=alkyl, aryl, alkaryl, aralkyl), nitro, nitroso, alkylsulfanyl, arylsulfanyl, alkylsulfinyl, arylsulfinyl, alkylsulfonyl, boronato (—B(OR)$_2$ where R is alkyl or other hydrocarbyl); or (R')$_p$ comprises an optionally substituted fused methylene linked diether, ethylene linked diether, or propylene linked diether, aryl or heteroaryl moiety; and
R'' is an amine protecting group or an optionally substituted alkyl, aryl, heteroaryl, alkaryl or alkheteroaryl.

13. The method of claim 1, wherein the organic substrate comprises at least one of the following moieties:

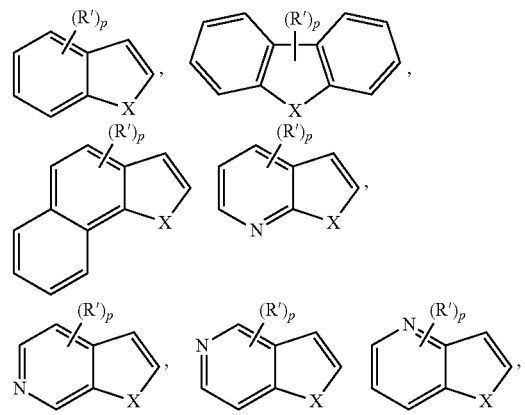

-continued

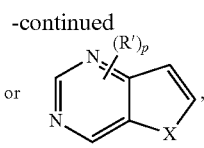

where X is N—R'', O, or S;
p is 0, 1, 2, or 3;
R' is a halo, hydroxyl, sulfhydryl, alkoxy, aryloxy, aralkyloxy, alkaryloxy, acyl, acyloxy, alkoxycarbonyl, aryloxycarbonyl, halocarbonyl, alkylcarbonato, arylcarbonato, carboxylato (—COO—), dialkyl-substituted carbamoyl, di haloalkyl-substituted carbamoyl, di aryl-substituted carbamoyl, di-alkyl-substituted thiocarbamoyl, di-aryl-substituted thiocarbamoyl, di-N-alkyl,N-aryl-substituted thiocarbamoyl, cyano, cyanato, thiocyanato, di-alkyl-substituted amino, di-aryl-substituted amino, arylimino (—CR=N(aryl), where R=alkyl, aryl, alkaryl, aralkyl), nitro, nitroso, alkylsulfanyl, arylsulfanyl, alkylsulfinyl, arylsulfinyl, alkylsulfonyl, boronato (—B(OR)$_2$ where R is alkyl or other hydrocarbyl); or (R')$_p$ comprises an optionally substituted fused methylene linked diether, ethylene linked diether, or propylene linked diether, aryl or heteroaryl moiety; and
R'' is an amine protecting group or an optionally substituted alkyl, aryl, heteroaryl, alkaryl or alkheteroaryl.

14. The method of claim 12, wherein the organic substrate comprises a heteroaryl moiety of structure:

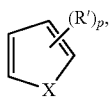

wherein p is 0, 1, or 2 and the silylation occurs at the C-2 position of the heteroaryl ring.

15. The method of claim 1, wherein the organic substrate comprises a heteroaryl moiety of structure:

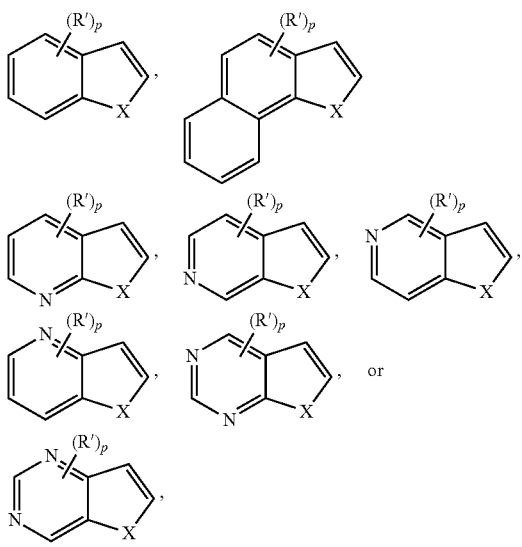

wherein p is 0, 1, or 2.

16. The method of claim 1, wherein the organic substrate is polymeric, oligomeric, or a polymeric precursor.

17. The method of claim 1, wherein the heteroaromatic silylated product is further reacted under conditions sufficient to couple the heteroaromatic silylated product with a second aromatic compound to form a biaromatic product, the method resulting in the formation of the biaromatic product.

18. The method of claim 1, wherein the heteroaromatic silylated product is further reacted under conditions sufficient to convert the heteroaromatic silylated product to a hydroxylated or alkoxylated or alkyl or aryl carboxylated product, the method resulting in the formation of the hydroxylated or aryloxylated or alkyl or aryl carboxylated product.

19. The method of claim 1, wherein the heteroaromatic silylated product is further reacted under conditions sufficient to convert the heteroaromatic silylated product to a heteroaromatic alpha-olefin product, the method resulting in the formation of the heteroaromatic alpha-olefin product.

20. The method of claim 1, wherein the heteroaromatic silylated product is further reacted under conditions sufficient to convert the heteroaromatic silylated product to a heteroaromatic chloro, bromo, fluoro, iodo, nitrate, or nitrite, the method resulting in the formation of the heteroaromatic chloro, bromo, fluoro, iodo, nitrate, or nitrite product.

21. The method of claim 1, wherein the heteroaromatic silylated product is further reacted under conditions sufficient to convert the heteroaromatic silylated product to a heteroaromatic boronic halide or boronic ester, the method resulting in the formation of the heteroaromatic boronic halide boronic ester.

22. The method of claim 1, where the organic substrate comprises a thiophene, wherein the heteroaromatic silylated product is a silylated thiophene product and the silylated thiophene product is further reacted under conditions sufficient to convert the silylated thiophene product to an alternating thiophene-perfluoroarene copolymer, the method resulting in the formation of the alternating thiophene-perfluoroarene copolymer.

23. A composition comprising:
(a) an organic substrate comprising a heteroaromatic moiety and a silylated derivative thereof, said silylated derivative having a C—Si bond in a position corresponding to a position in the heteroaromatic moiety of the organic substrate having a C—H bond;
(b) at least one organodisilane; and
(c) at least one potassium alkoxide base.

24. The method of claim 1, wherein the organic solvent comprises a non-tertiary ether or an alkylphosphoramide solvent.

25. The method of claim 1, wherein the organic solvent comprises hexamethylphosphoramide (HMPA), tetrahydrofuran (THF), 2-methyl-THF, or a dioxane.

26. The composition of claim 23, further comprising an organic solvent having an oxygen donor group.

27. The composition of claim 26, wherein the organic solvent comprises a non-tertiary ether or an alkylphosphoramide solvent.

28. The composition of claim 26, wherein the organic solvent comprises hexamethylphosphoramide (HMPA), tetrahydrofuran (THF), 2-methyl-THF, or a dioxane.

29. The composition of claim 23, wherein the composition is substantially free of transition-metal compounds.

30. The composition of claim 23, wherein at least one organodisilane comprises an organodisilane of Formula (I):

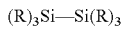 (I)

wherein:
  each R is independently H, optionally substituted $C_{1-12}$ alkyl or $C_{1-12}$ heteroalkyl, optionally substituted $C_{6-20}$aryl or $C_{5-20}$heteroaryl, optionally substituted $C_{7-30}$alkaryl or $C_{6-30}$ heteroalkaryl, optionally substituted $C_{7-30}$ aralkyl or $C_{6-30}$heteroaralkyl, optionally substituted —O—$C_{1-12}$ alkyl or —O—$C_{1-12}$ heteroalkyl, optionally substituted —O—$C_{6-20}$ aryl or —O—$C_{5-20}$ heteroaryl, optionally substituted —O—$C_{7-30}$ alkaryl or —O—$C_{6-30}$ heteroalkaryl, optionally substituted —O—$C_{7-30}$ alkaryl or —O—$C_{6-30}$ heteroaralkyl, or optionally substituted —O—$C_{7-30}$ aralkyl or —O—$C_{6-30}$ heteroaralkyl, and, if substituted, the substituents are phosphonato, phosphoryl, phosphanyl, phosphino, sulfonato, $C_1$-$C_{20}$ alkylsulfanyl, $C_6$-$C_{20}$ arylsulfanyl, $C_1$-$C_{20}$ alkylsulfonyl, $C_6$-$C_{20}$ arylsulfonyl, $C_1$-$C_{20}$ alkylsulfinyl, $C_6$-$C_{20}$ arylsulfinyl, sulfonamido, amino, amido, imino, nitro, nitroso, hydroxyl, $C_1$-$C_{20}$ alkoxy, $C_6$-$C_{20}$ aryloxy, $C_2$-$C_{20}$ alkoxycarbonyl, $C_6$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, or where the substituents may optionally provide a tether to an insoluble or sparingly soluble support media comprising alumina, silica, or carbon.

31. The composition of claim 30, wherein each R is independently $C_{1-6}$ alkyl.

32. The composition of claim 30, wherein at least one R is H.

33. The composition of claim 23, wherein the at least one potassium alkoxide base comprises a $C_{1-12}$ linear or branched alkyl moiety or a $C_{6-10}$ aryl or $C_{5-10}$ heteroaryl moiety.

34. The composition of claim 23, wherein the at least one potassium alkoxide base comprises potassium methoxide, potassium ethoxide, potassium propoxide, potassium butoxide, or 2-ethyl-hexyl alkoxide.

35. The composition of claim 23, where the at least one organodisilane is hexamethyldisilane or hexa-ethyldisilane and at least one potassium alkoxide base is potassium methoxide, potassium ethoxide, or potassium tert-butoxide.

36. The composition of claim 23, wherein the at least one organodisilane and the at least one potassium alkoxide base are present together at a molar ratio, with respect to one another, in a range of from about 20:1 to about 1:1.

37. The composition of claim 23, wherein the at least one potassium alkoxide base and organic substrate are present together at a molar ratio, with respect to one another, in a range of from about 0.01:1 to about 0.9:1.

38. The composition of claim 23, wherein the organic substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, pyridine, or a dibenzothiophene.

39. The composition of claim 23, wherein the organic heteroaromatic substrate comprises at least one of the following moieties:

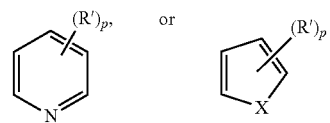

where X is N—R'', O, or S;
  p is 0, 1, 2, or 3;
  R' is a halo, hydroxyl, sulfhydryl, alkoxy, aryloxy, aralkyloxy, alkaryloxy, acyl, acyloxy, alkoxycarbonyl, aryloxycarbonyl, halocarbonyl, alkylcarbonato, arylcarbonato, carboxylato (—COO—), dialkyl-substituted carbamoyl, di-haloalkyl-substituted carbamoyl, di aryl-substituted carbamoyl, di-alkyl-substituted thiocarbamoyl, di-aryl-substituted thiocarbamoyl, di-N-alkyl),N-aryl-substituted thiocarbamoyl, cyano, cyanato, thiocyanato, di-alkyl-substituted amino, di-aryl-substituted amino, arylimino (—CR=N(aryl), where R=alkyl, aryl, alkaryl, aralkyl, nitro, nitroso, alkylsulfanyl, arylsulfanyl, alkylsulfinyl, arylsulfinyl, alkylsulfonyl, boronato (—B(OR)$_2$ where R is alkyl or other hydrocarbyl); or (R')$_p$ comprises an optionally substituted fused methylene linked diether, ethylene linked diether, or propylene linked diether, aryl or heteroaryl moiety; and
  R'' is an amine protecting group or an optionally substituted alkyl, aryl, heteroaryl, alkaryl or alkheteroaryl.

40. The composition of claim 23, wherein the organic substrate comprises at least one of the following moieties:

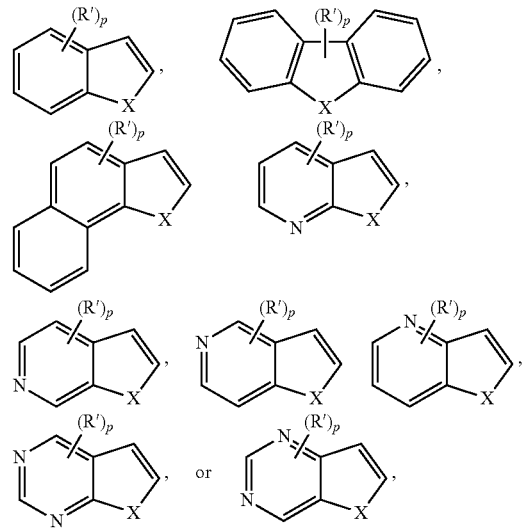

where X is N—R'', O, or S;
  p is 0, 1, 2, or 3;
  R' is a halo, hydroxyl, sulfhydryl, alkoxy, aryloxy, aralkyloxy, alkaryloxy, acyl, acyloxy, alkoxycarbonyl, aryloxycarbonyl, halocarbonyl, alkylcarbonato, arylcarbonato, carboxylato (—COO—), dialkyl-substituted carbamoyl, di haloalkyl-substituted carbamoyl, di, aryl-substituted carbamoyl, di-alkyl-substituted thiocarbamoyl, di-aryl-substituted thiocarbamoyl, di-N-alkyl,N-aryl-substituted thiocarbamoyl, cyano, cyanato, thiocyanato, di-alkylsubstituted amino, di-aryl-substituted amino, arylimino (—CR═N(aryl), where R═alkyl, aryl, alkaryl, aralkyl), nitro, nitroso, alkylsulfanyl, arylsulfanyl, alkylsulfinyl, arylsulfinyl, alkylsulfonyl, boronato (—B(OR)$_2$ where R is alkyl or other hydrocarbyl); or (R')$_p$ comprises an optionally substituted fused methylene linked diether, ethylene linked diether, or propylene linked diether, aryl or heteroaryl moiety; and R" is an amine protecting group or an optionally substituted alkyl, aryl, heteroaryl, alkaryl or alkheteroaryl.

41. The composition of claim 39, wherein the organic substrate comprises a heteroaryl moiety of structure:

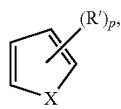

where p is 0, 1, or 2.

42. The composition of claim 41, wherein the silylated derivative of the organic substrate is present and contains a silyl group in the C-2 or C-3 position of the heteroaryl moiety.

43. The composition of claim 40, wherein the organic substrate comprises a heteroaryl moiety of structure:

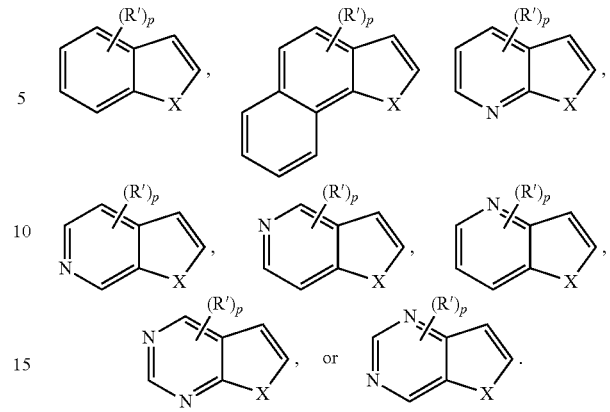

where p is 0, 1, or 2.

44. The composition of claim 43, wherein the silylated derivative of the organic substrate is present and contains a silyl group in the C-2 or C-3 position of the 5-membered heteroaryl ring.

45. The composition of claim 23, wherein the organic substrate is polymeric, oligomeric, or a polymeric precursor.

46. The composition of claim 23, wherein the silylated derivative of the organic substrate is present.

* * * * *